United States Patent
Viswanathan et al.

(10) Patent No.: US 11,020,180 B2
(45) Date of Patent: Jun. 1, 2021

(54) EPICARDIAL ABLATION CATHETER

(71) Applicant: Farapulse, Inc., Menlo Park, CA (US)

(72) Inventors: Raju Viswanathan, Mountain View, CA (US); Jean-Luc Pageard, Montreal (CA)

(73) Assignee: Farapulse, Inc., Menlo Park, CA (US)

( * ) Notice: Subject to any disclaimer, the term of this patent is extended or adjusted under 35 U.S.C. 154(b) by 0 days.

(21) Appl. No.: 17/091,221

(22) Filed: Nov. 6, 2020

(65) Prior Publication Data

US 2021/0052325 A1 Feb. 25, 2021

Related U.S. Application Data

(63) Continuation of application No. PCT/US2019/030882, filed on May 6, 2019.
(Continued)

(51) Int. Cl.
*A61B 18/18* (2006.01)
*A61B 18/14* (2006.01)
*A61B 18/00* (2006.01)

(52) U.S. Cl.
CPC .............. *A61B 18/1492* (2013.01); *A61B 2018/00166* (2013.01); *A61B 2018/00363* (2013.01);
(Continued)

(58) Field of Classification Search
CPC ...... A61B 18/1492; A61B 2018/00577; A61B 2018/00613; A61B 2018/1467;
(Continued)

(56) References Cited

U.S. PATENT DOCUMENTS

| 4,200,104 A | 4/1980 | Harris |
| 4,470,407 A | 9/1984 | Hussein |

(Continued)

FOREIGN PATENT DOCUMENTS

| EP | 1042990 A1 | 10/2000 |
| EP | 1125549 | 8/2001 |

(Continued)

OTHER PUBLICATIONS

International Search Report and Written Opinion for International Application No. PCT/US2019/030882, dated Sep. 10, 2019, 17 pages.
(Continued)

*Primary Examiner* — Michael F Peffley
*Assistant Examiner* — Amanda L Zink
(74) *Attorney, Agent, or Firm* — Cooley LLP

(57) ABSTRACT

Systems, devices, and methods for electroporation ablation therapy are disclosed herein, with a cinch device for positioning an ablation catheter relative to tissue during a cardiac ablation procedure. In some embodiments, a distal end of a first device may be advanced into a proximal end of a first lumen of a second device. The first device may be advanced from a distal end of the first lumen and the first device may be looped around tissue of a patient. The first device may be advanced into a distal end of a second lumen of the second device. The distal end of the first device may be advanced from a proximal end of the second lumen. The proximal and distal ends of the first device may be advanced away from a proximal end of the second device to increase contact between the first device and the tissue.

30 Claims, 15 Drawing Sheets

Related U.S. Application Data

(60) Provisional application No. 62/667,964, filed on May 7, 2018.

(52) U.S. Cl.
CPC .............. *A61B 2018/00375* (2013.01); *A61B 2018/00577* (2013.01); *A61B 2018/00613* (2013.01); *A61B 2018/1407* (2013.01); *A61B 2018/1467* (2013.01)

(58) Field of Classification Search
CPC ........... A61B 2018/00357; A61B 2018/00267; A61B 2018/00351; A61B 2018/00363; A61B 2018/00154; A61B 2018/0016; A61B 2018/1497; A61B 18/14; A61B 2018/00404; A61B 2017/00477; A61B 2018/1475

See application file for complete search history.

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,913,854 A | 6/1999 | Maguire et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |

(56) References Cited

U.S. PATENT DOCUMENTS

| | | |
|---|---|---|
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harley et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,568,410 B2 | 10/2013 | Vakharia et al. |
| 8,571,635 B2 | 10/2013 | McGee |
| 8,571,647 B2 | 10/2013 | Harlev et al. |
| 8,579,897 B2 | 11/2013 | Vakharia et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 * | 8/2014 | Emmons .............. A61B 18/18 606/33 |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,610,118 B2 * | 4/2017 | Olson .............. A61B 5/6852 |
| 9,700,368 B2 | 7/2017 | Callas et al. |
| 9,724,170 B2 | 8/2017 | Mickelsen |
| 9,757,193 B2 | 9/2017 | Zarins et al. |

(56) References Cited

U.S. PATENT DOCUMENTS

| | | |
|---|---|---|
| 9,782,099 B2 | 10/2017 | Williams et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,130,423 B1 | 11/2018 | Viswanathan et al. |
| 10,172,673 B2 | 1/2019 | Viswanathan et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 10,624,693 B2 | 4/2020 | Mickelsen et al. |
| 10,835,314 B2 | 11/2020 | Long et al. |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Christian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0208185 A1 | 8/2011 | Diamant et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |

(56) References Cited

U.S. PATENT DOCUMENTS

| | | |
|---|---|---|
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |

(56) References Cited

U.S. PATENT DOCUMENTS

| | | |
|---|---|---|
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0168511 A1 | 6/2018 | Hall et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0303488 A1 | 10/2018 | Hill |
| 2018/0311497 A1 | 11/2018 | Viswanathan et al. |
| 2018/0344393 A1 | 12/2018 | Gruba et al. |
| 2018/0360534 A1 | 12/2018 | Teplitsky et al. |
| 2019/0069950 A1 | 3/2019 | Viswanathan et al. |
| 2019/0151015 A1 | 5/2019 | Viswanathan et al. |
| 2019/0183378 A1 | 6/2019 | Mosesov et al. |
| 2019/0231421 A1 | 8/2019 | Viswanathan et al. |
| 2019/0269912 A1 | 9/2019 | Viswanathan et al. |
| 2019/0336198 A1 | 11/2019 | Viswanathan et al. |
| 2019/0336207 A1 | 11/2019 | Viswanathan |

FOREIGN PATENT DOCUMENTS

| | | |
|---|---|---|
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |
| EP | 2777579 A1 | 9/2014 |
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/093926 | 6/2017 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/218734 | 12/2017 |
| WO | WO 2018/005511 | 1/2018 |
| WO | WO 2018/200800 | 11/2018 |
| WO | WO 2019/133606 | 7/2019 |

OTHER PUBLICATIONS

Office Action for Canadian Application No. 2,881,462, dated Mar. 19, 2019, 5 pages.
Partial Supplementary European Search Report for European Application No. 13827672.0, dated Mar. 23, 2016, 6 pages.
Supplementary European Search Report for European Application No. 13827672.0, dated Jul. 11, 2016, 12 pages.
Office Action for European Application No. 13827672.0, dated Feb. 5, 2018, 6 pages.
Notice of Reasons for Rejection for Japanese Application No. 2015-526522, dated Mar. 6, 2017, 3 pages.

(56) References Cited

OTHER PUBLICATIONS

Office Action for U.S. Appl. No. 14/400,455, dated Mar. 30, 2017, 10 pages.
International Search Report and Written Opinion for International Application No. PCT/US2013/031252, dated Jul. 19, 2013, 12 pages.
Extended European Search Report for European Application No. 19182099.2, dated Dec. 13, 2019, 7 pages.
Office Action for Japanese Application No. 2018-036714, dated Jan. 16, 2019, 8 pages.
Office Action for Japanese Application No. 2018-036714, dated Nov. 27, 2019, 5 pages.
Office Action for U.S. Appl. No. 15/819,726, dated Jun. 4, 2018, 17 pages.
Office Action for U.S. Appl. No. 15/917,194, dated Jun. 4, 2018, 17 pages.
Office Action for U.S. Appl. No. 15/917,194, dated Oct. 9, 2018, 13 pages.
Office Action for U.S. Appl. No. 15/917,194, dated Apr. 29, 2019, 10 pages.
Office Action for U.S. Appl. No. 15/917,194, dated Dec. 20, 2019, 10 pages.
First Office Action for Chinese Application No. 201580006848.8, dated Jan. 29, 2018, 15 pages.
Office Action for European Application No. 15701856.5, dated Dec. 11, 2017, 6 pages.
Notice of Reasons for Rejection for Japanese Application No. 2016-544072, dated Oct. 1, 2018, 11 pages.
Office Action for U.S. Appl. No. 15/201,983, dated Apr. 3, 2019, 16 pages.
Office Action for U.S. Appl. No. 15/201,983, dated Nov. 15, 2019, 15 pages.
International Search Report and Written Opinion for International Application No. PCT/US2015/010138, dated Mar. 26, 2015, 14 pages.
International Preliminary Report on Patentability for International Application No. PCT/US2015/010138, dated Jul. 12, 2016, 9 pages.
Extended European Search Report for European Application No. 15849844.4, dated May 3, 2018, 8 pages.
Office Action for U.S. Appl. No. 15/484,969, dated Sep. 4, 2019, 12 pages.
Office Action for U.S. Appl. No. 15/484,969, dated Jul. 16, 2020, 12 pages.
International Search Report and Written Opinion for International Application No. PCT/US2015/055105, dated Mar. 1, 2016, 15 pages.
Office Action for U.S. Appl. No. 15/796,255, dated Jan. 10, 2018, 12 pages.
Extended European Search Report for European Application No. 15806855.1, dated Jan. 3, 2018, 8 pages.
Office Action for U.S. Appl. No. 15/354,475, dated May 23, 2019, 7 pages.
International Search Report and Written Opinion for International Application No. PCT/US2015/035582, dated Oct. 2, 2015, 17 pages.
Office Action for U.S. Appl. No. 15/970,404, dated Oct. 9, 2018, 21 pages.
Office Action for U.S. Appl. No. 15/970,404, dated Apr. 12, 2019, 20 pages.
Office Action for U.S. Appl. No. 15/970,404, dated Nov. 12, 2019, 19 pages.
International Search Report and Written Opinion for International Application No. PCT/US2019/028943, dated Sep. 17, 2019, 17 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for U.S. Appl. No. 17/087,433, dated Dec. 23, 2020, 14 pages.

\* cited by examiner

EPICARDIAL ABLATION CATHETER

CROSS-REFERENCE TO RELATED APPLICATIONS

This application is a continuation of International Application No. PCT/US2019/030882, filed on May 6, 2019, which claims the benefit of U.S. Provisional Application No. 62/667,964, filed on May 7, 2018, the entire disclosure of each of which is incorporated herein by reference in its entirety.

BACKGROUND

The generation of pulsed electric fields for tissue therapeutics has moved from the laboratory to clinical applications over the past two decades, while the effects of brief pulses of high voltages and large electric fields on tissue have been investigated for the past forty years or more. Application of brief high direct current (DC) voltages to tissue may generate locally high electric fields typically in the range of hundreds of volts per centimeter that disrupt cell membranes by generating pores in the cell membrane. While the precise mechanism of this electrically-driven pore generation or electroporation continues to be studied, it is thought that the application of relatively brief and large electric fields generates instabilities in the lipid bilayers in cell membranes, causing the occurrence of a distribution of local gaps or pores in the cell membrane. This electroporation may be irreversible if the applied electric field at the membrane is larger than a threshold value such that the pores do not close and remain open, thereby permitting exchange of biomolecular material across the membrane leading to necrosis and/or apoptosis (cell death). Subsequently, the surrounding tissue may heal naturally. While pulsed DC voltages may drive electroporation under the right circumstances, there remains an unmet need for thin, flexible, atraumatic devices that effectively deliver high DC voltage electroporation ablation therapy selectively to cardiac tissue in regions of interest.

BRIEF SUMMARY

Described here are systems, devices, and methods for ablating tissue through irreversible electroporation. In some embodiments, a system may comprise an ablation device including a proximal portion, a distal portion, and a central portion, the central portion including a set of electrodes disposed thereon. A cinch device may define a first lumen configured to slidably receive the proximal portion of the ablation device and a second lumen may extend parallel to the first lumen and be configured to slidably receive the distal portion of the ablation device, such that the central portion of the ablation device forms an adjustable loop when the proximal and distal portions of the ablation device are received in the first and second lumens of the cinch device.

In some embodiments, the set of electrodes may include subsets of electrodes, each subset of electrodes has a first length, and adjacent subsets of electrodes are spaced from each other by a second length. In some of these embodiments, the set of electrodes includes between about 4 electrode subsets and about 20 electrode subsets.

In some embodiments, the ablation device may include first and second sets of fiducials. Fiducials of the first and second sets of fiducials may be alternately disposed along a length of the ablation device, and the first set of fiducials differs from the second set of fiducials by one or more characteristics. In some of these embodiments, adjacent fiducials of the first set of fiducials are spaced apart by a sum of the first and second lengths. In some embodiments, the first and second set of fiducials may be disposed along at least one of the proximal and distal portions of the ablation device. In some embodiments, the one or more characteristics may include at least one of: a length, a thickness, a depth, a shape, a color, a pattern, an orientation, a texture, or a material.

In some embodiments, a fiducial of the first set of fiducials is spaced from an adjacent fiducial of the second set of fiducials by a third length equal to a width of an electrode of the set of electrodes. In some embodiments, the cinch device may have a fourth length being an integer multiple of a sum of the first and second lengths. In some embodiments, each subset of electrodes includes a plurality of electrodes, each electrode of the plurality of electrodes having a third length and being spaced from an adjacent electrode of the plurality of electrodes by a distance. The ablation device including a set of fiducials with spacing between adjacent proximal fiducials may alternate between a fourth length equal to the third length and a fifth length equal to the distance.

In some embodiments, each subset of electrodes may include a plurality of electrodes, a first electrode of the plurality of electrodes having a third length and a second electrode of the plurality of electrodes having a fourth length greater than the third length. The ablation device may include first and second sets of fiducials alternately disposed along a length of the ablation device, with a fiducial of the first set of fiducials being spaced from an adjacent fiducial of the second set of fiducials by the third length.

In some embodiments, the ablation device may be configured to transition between a first configuration in which the ablation device extends linearly and a second configuration in which the central portion of the ablation device forms the adjustable loop. In some embodiments, the adjustable loop may be configured to be positioned around a set of pulmonary veins of a heart. In some embodiments, the set of electrodes may be configured to generate a pulsed electric field to ablate cardiac tissue in response to receiving a voltage pulse waveform. In some embodiments, the ablation device may include a handle coupled to a proximal end of the proximal portion of the ablation device.

In some embodiments, the ablation device may be a catheter including a guidewire lumen configured to receive a guidewire, such that the catheter can be positioned around a set of pulmonary veins of a heart using a guidewire. In some embodiments, a lock may be configured to hold the ablation device in place relative to the cinch device. In some embodiments, each electrode of the set of electrodes may include a length of between about 1 mm and about 12 mm. In some embodiments, the distal portion of the ablation device may have a length of between about 20 cm and about 70 cm.

In some embodiments, an apparatus may comprise an elongate shaft defining first and second lumens extending parallel to one another, the first and second lumens configured to slidably receive opposite ends of an ablation catheter such that the ablation catheter forms an adjustable loop extending from the elongate shaft when the opposite ends of the ablation catheter are received within the first and second lumens, the elongate shaft including a proximal portion defining a longitudinal axis and a distal portion having a curvature relative to the longitudinal axis of the proximal portion.

In some embodiments, the curvature of the distal portion may be between about 30 degrees and about 60 degrees relative to the longitudinal axis of the proximal portion. In some embodiments, the elongate shaft may have a length of between about 6 cm and about 30 cm. In some embodiments, at least a distal end of the elongate shaft may be configured to be visualized fluoroscopically. In some embodiments, the first and second lumens have the same diameter. In some embodiments, the first and second lumens may be configured to slidably receive a portion of the ablation device having one or more electrodes disposed thereon. In some embodiments, the first and second lumens may be configured to slidably receive the opposite ends of the ablation catheter such that at least one of the opposite ends of the ablation device can be moved relative to the elongate shaft to adjust a positioning of the adjustable loop around a portion of a heart. In some embodiments, at least a portion of the tubular shaft is configured to be disposed within a pericardial space.

In some embodiments, a method may comprise advancing a distal end of an ablation device through a first lumen of a cinch device in a proximal-to-distal direction. The ablation device may be positioned around cardiac tissue of a heart of a subject such that the ablation device forms an adjustable loop that circles around a set of pulmonary veins of the heart. The distal end of the ablation device may be advanced through a second lumen of the cinch device in a distal-to-proximal direction. The second lumen may extend substantially parallel to the first lumen. At least one of the distal end or a proximal end of the ablation device may be moved proximally from a proximal end of the cinch device to reduce a size of the adjustable loop and increase contact between the ablation device and the cardiac tissue.

In some embodiments, the adjustable loop of the ablation device extends through a pericardial reflection of the heart. In some embodiments, moving the at least one of the distal or proximal ends of the ablation device proximally from a proximal end of the cinch device applies a predetermined force via the ablation device to the cardiac tissue. In some embodiments, the method may further comprise advancing the cinch device into a pericardial space of the subject. In some embodiments, the method may further comprise positioning the cinch device on a posterior side of the heart. In some embodiments, the method may further comprise positioning the cinch device such that the clinch device is angled obliquely relative to a chest of the subject. In some embodiments, the method may further comprise locking a position of the ablation device relative to the cinch device after moving the at least one of the distal or proximal end of the ablation device. In some embodiments, the method may further comprise delivering, via a set of electrodes of the ablation device, a pulsed electric field to the cardiac tissue to ablate the cardiac tissue.

In some embodiments, a method may comprise advancing a distal end of an ablation device through a first lumen of a cinch device in a proximal-to-distal direction. The ablation device may be positioned around cardiac tissue of a heart of a subject such that the ablation device forms an adjustable loop that circles around a set of pulmonary veins of the heart. The distal end of the ablation device may be advanced through a second lumen of the cinch device in a distal-to-proximal direction, the second lumen extending substantially parallel to the first lumen. A position of a set of electrodes of the ablation device may be verified relative to the cinch device based at least on a set of fiducials disposed on at least one of a distal or proximal portion of the ablation device.

In some embodiments, the method may further comprise visualizing one or more fiducials of the set of fiducials of the ablation device disposed on a portion of the ablation device disposed outside of the cinch device. In some embodiments, verifying a position of the set of electrodes of the ablation device includes identifying, using the set of fiducials, at least one electrode of the set of electrodes disposed distal to the cinch device. In some embodiments, the method may further comprise applying a pulse waveform to the at least one electrode disposed distal to the cinch device and not to remaining electrodes of the set of electrodes.

DETAILED DESCRIPTION

Figure 1:
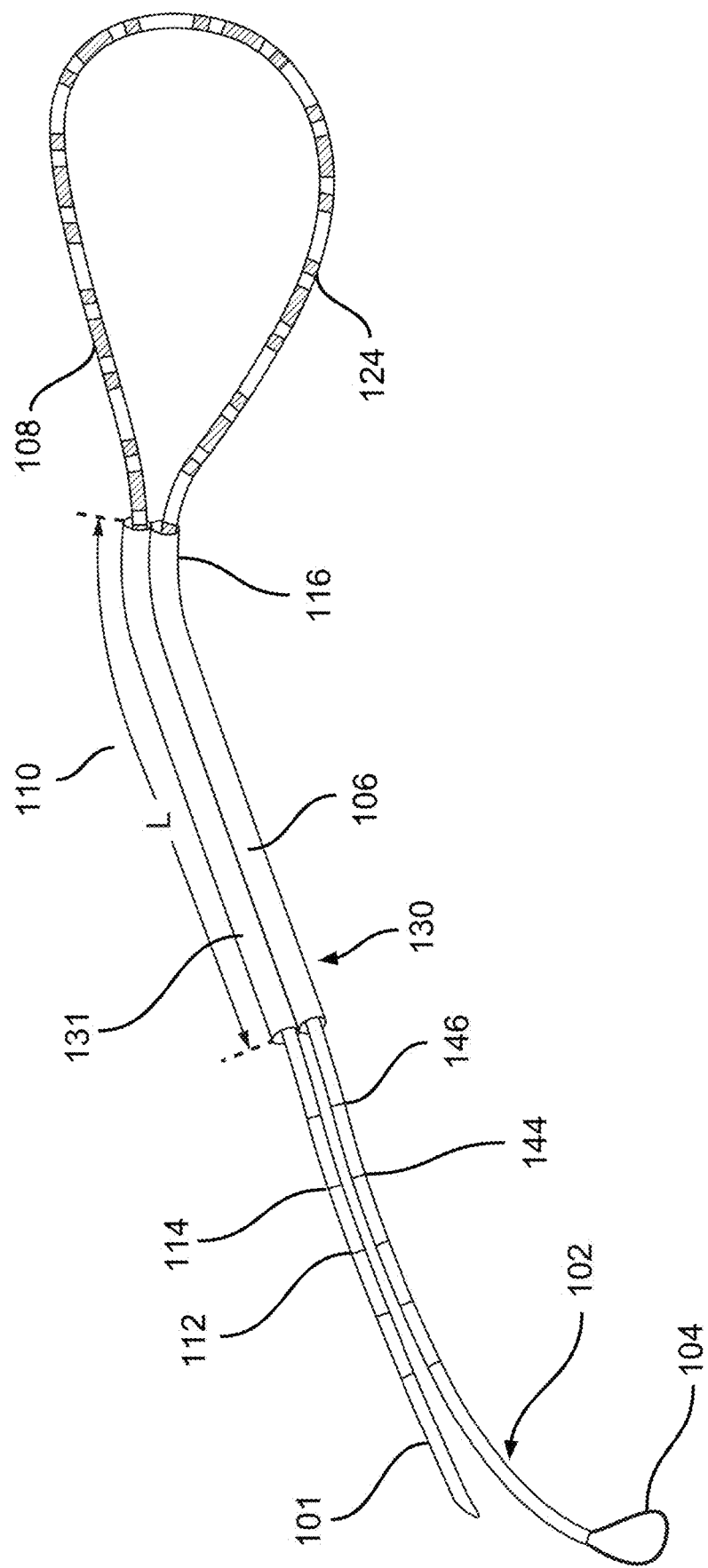
FIG. 1 is a perspective view of an ablation device and a cinch device, according to embodiments.

Described herein are systems, devices, and methods for selective and rapid application of pulsed electric fields to ablate tissue by irreversible electroporation. Generally, the systems, devices, and methods described herein may be used to generate large electric field magnitudes at desired regions of interest and reduce peak electric field values elsewhere in order to reduce unintended tissue damage. The devices described herein include flexible catheters that may be placed for pulsed electric field ablation of cardiac tissue. In some embodiments, an ablation device may be placed via subxiphoid access or by direct surgical placement into the pericardial space. Proper physical placement and tension applied between an ablation device (e.g., ablation catheter) and tissue to be ablated may ensure targeted and effective electroporation with reduced side effects and user error. For example, a cinch device and fiducials disposed thereon may be used to aid in positioning and verification of positioning of an ablation device relative to target tissue.

An irreversible electroporation system as described herein may include a signal generator and a processor configured to apply one or more voltage pulse waveforms to a selected set of electrodes of an ablation device to deliver energy to a region of interest (e.g., ablation energy for tissue in a pulmonary vein ostium) and in one embodiment provide a highly configurable set of electrode channels (e.g., allow independent and arbitrary electrode selection). In some embodiments, while electrodes to be activated and/or electrodes for non-activation are selectable, electrode pairings (e.g., anode-cathode subsets) may be automatically configured based on the activated electrodes. The pulse waveforms disclosed herein may aid in therapeutic treatment of a variety of cardiac arrhythmias (e.g., atrial fibrillation). In order to deliver the pulse waveforms generated by the signal generator, one or more electrodes of the ablation device may have an insulated electrical lead configured for sustaining a voltage potential of at least about 700 V without dielectric breakdown of its corresponding insulation. Subsets of electrodes may be independently addressable such that the subset may be controlled (e.g., deliver energy) independently of any other electrode of the device. In this manner, the electrodes and/or electrode subsets may deliver different energy waveforms with different timing synergistically for electroporation of tissue.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in International Application Serial No. PCT/US2016/057664, filed on Oct. 19, 2016, and titled "SYSTEMS, APPARATUSES AND METHODS FOR DELIVERY OF ABLATIVE ENERGY TO TISSUE," and as described in U.S. Provisional Patent Application No. 62/733,968, filed on Sep. 20, 2018, and titled "SYSTEMS, APPARATUSES AND METHODS FOR DELIVERY OF ABLATIVE ENERGY TO TISSUE," the contents of which are hereby incorporated by reference in their entirety.

In some embodiments, the systems may further include a cardiac stimulator used to synchronize the generation of the pulse waveform to a paced heartbeat. The cardiac stimulator may electrically pace the heart with a cardiac stimulator and ensure pacing capture to establish periodicity and predictability of the cardiac cycle. A time window within a refractory period of the periodic cardiac cycle may be selected for voltage pulse waveform delivery. Thus, voltage pulse waveforms may be delivered in the refractory period of the cardiac cycle so as to avoid disruption of the sinus rhythm of the heart. In some embodiments, the system may optionally include one or more return electrodes. In some embodiments, cardiac stimulator functionality may be integrated into a signal generator (e.g., ablation console, waveform generator console).

Generally, to ablate tissue, one or more catheters may be advanced to a target location. In a cardiac application, the electrodes through which the voltage pulse waveform is delivered may be disposed on an epicardial device. The methods described here may include introducing an ablation catheter through a first lumen of a cinch device. The ablation catheter may be advanced out of the first lumen and looped around cardiac tissue such as a set of pulmonary veins. The distal end of the ablation catheter may be advanced back into the cinch device through a distal end of a second lumen. The ablation catheter may then be advanced out of the proximal end of the cinch device such that the proximal and distal ends of the ablation catheter are on the proximal side of the ablation catheter. The ends of the ablation catheter may be pulled away from the cinch device held in place such that the loop of the ablation catheter tightens around the tissue to increase contact and apply a predetermined force. A position of the ablation catheter relative to the cinch device may be verified using a set of fiducials disposed on the ablation catheter and/or cinch device. For example, one or more electrodes and/or one or more subsets of electrodes may be disposed within a lumen of the cinch device. These electrodes may be non-activated for ablation.

A pulse waveform may be generated and delivered to one or more identified electrodes of the ablation catheter (e.g., electrodes uncovered by the cinch device) to ablate tissue. In some embodiments, the pulse waveform may be generated in synchronization with a pacing signal of the heart to avoid disruption of the sinus rhythm of the heart. In some embodiments, the electrodes may be configured in anode-cathode subsets. The pulse waveform may include hierarchical waveforms to aid in tissue ablation and reduce damage to healthy tissue.

Figure 14:
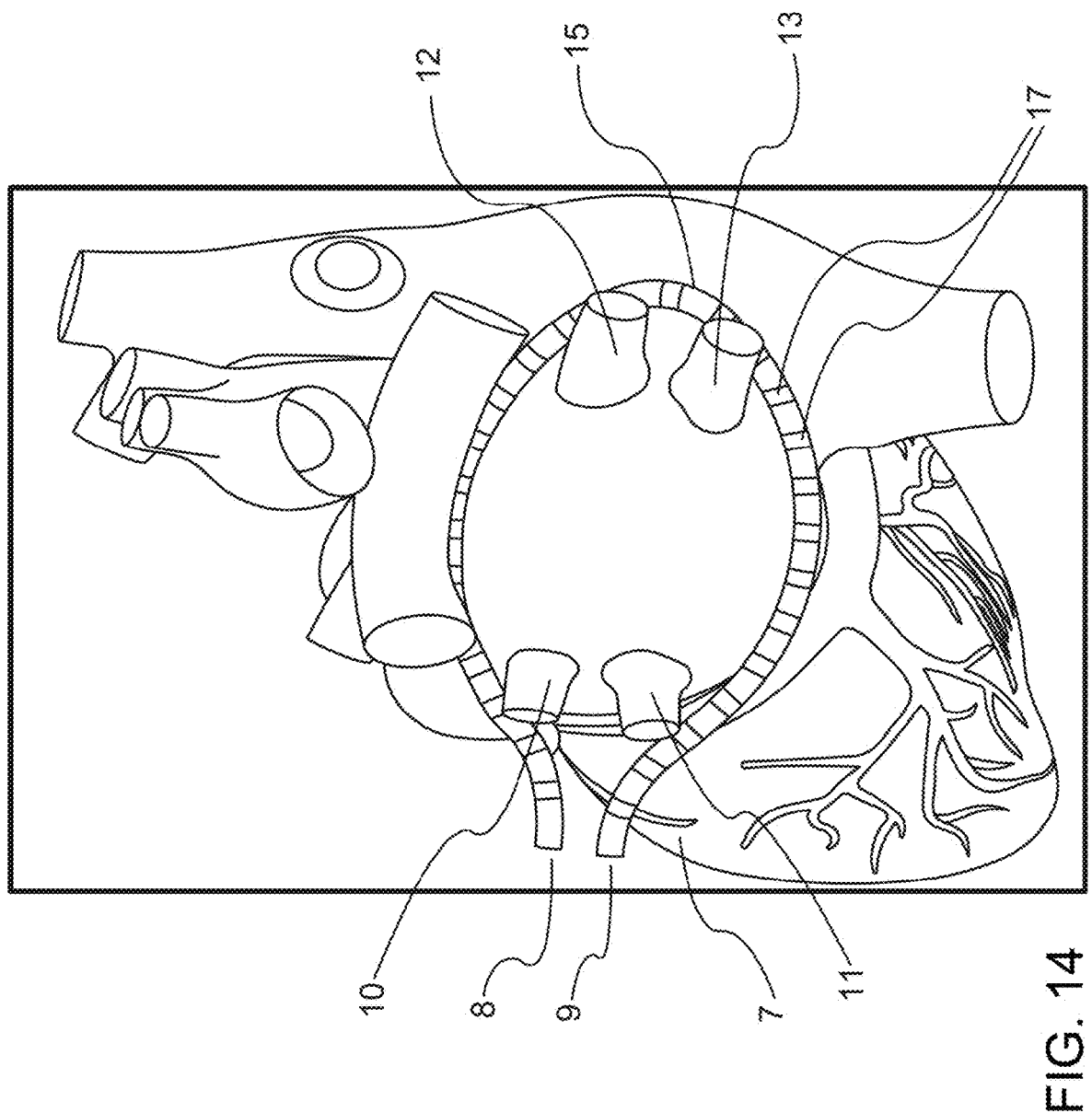
FIG. 14 is a perspective view of an ablation device according to embodiments, with the ablation device including multiple electrodes disposed along its shaft and wrapped around a portion of the pulmonary veins and being within the epicardial space of the heart in a subject body such that the ablation device forms an approximately closed contour around the pulmonary veins.

Generally, the systems and devices described herein include one or more catheters configured to ablate tissue in a left atrial chamber of a heart. As shown in FIG. 14, in some embodiments, a pulmonary vein isolation (PV isolation) system may include an ablation device (15) (e.g., ablation catheter), having a proximal portion (9) and a distal portion (8). The ablation device (15) may include a set of electrodes (17) disposed along its length, and where the ablation device (15) is wrapped in the epicardial space around all four pulmonary veins (10, 11, 12, 13) of a heart (7) in a subject or patient anatomy, with the proximal and distal portions (9) and (8) respectively of the ablation device (15) extending out and away to eventually emerge from the patient's chest. The ablation device (15) and any of the ablation devices described herein can be similar to the ablation catheters described in PCT Publication No. WO 2014/025394, entitled "Catheters, Catheter Systems, and Methods for Puncturing Through a Tissue Structure," filed on Mar. 14, 2013, as International Application Serial No. PCT/US2013/031252 ("the '394 PCT Application Publication), which is incorporated herein by reference in its entirety. The ablation device (15) may be disposed about the pulmonary veins (10, 11, 12, 13) using any suitable procedure and apparatus. For example, in some embodiments, the ablation devices may be disposed about the pulmonary veins (10, 11, 12, 13) and/or the heart (7) using a puncturing apparatus disposed via a subxiphoid pericardial access location and using guidewire-based delivery methods as described in the '394 PCT Application Publication and/or International Application Serial No. PCT/US2017/037609, filed on Jun. 15, 2017, which is incorporated herein by reference in its entirety. In some embodiments, as described in the '394 PCT Application Publication, delivery catheters having magnetic members configured to form a magnetic coupling across a pericardial reflection can be used to deliver a guidewire into position around a heart. Similar and/or alternative methods can be used to deliver and position the ablation device (15). An alternative placement method includes direct surgical placement in an open chest, such as during a surgical procedure. In some embodiments, after the ends (8) and (9) of the ablation device (15) extend and emerge out of the patient chest they can be cinched together using a cinch device, as described in more detail herein, to effectively hold the ablation devices in place or in stable position relative to each other.

In some embodiments, the ablation device (15) may be inserted into one end of a proximal end of a first lumen of a double-barreled cinch device, as described in detail herein, then pulled through the lumen, placed around the base of one or more pulmonary veins to form a loop around the pulmonary veins, and then inserted into a distal end of a second lumen of the cinch device such that a distal end of the ablation device (15) extends from the proximal end of the second lumen of the cinch device.

While FIG. 14 illustrates a single catheter system, the embodiments described herein may also apply to a two catheter system encircling the pulmonary veins such as described in International Application No. PCT/US2015/031086, entitled "METHODS AND APPARATUS FOR MULTI-CATHETER TISSUE ABLATION," filed on May 15, 2015, which is incorporated herein by reference in its entirety.

A voltage (e.g., DC voltage) for electroporation may be applied to subsets of electrodes identified as anodes and cathodes respectively on the two devices on approximately opposite sides of the closed contour defined by the shapes of the ablation device (15) around the pulmonary veins. The voltage may be applied in brief pulses sufficient to cause irreversible electroporation and may be in the range of 0.5 kV to 10 kV and more preferably in the range 1 kV to 2.5 kV, so that a threshold electric field value of around 200 Volts/cm may be effectively achieved in the cardiac tissue to be ablated. In some embodiments, the active electrodes on the two devices may be automatically and/or manually identified on an X-ray or fluoroscopic image obtained at an appropriate angulation that permits identification of the geometric distance between anode and cathode electrodes, or their respective centroids. For example, fiducials (not shown in FIG. 14 and as described in more detail herein) may be disposed on surfaces of one or more of the ablation device (15) and cinch device and may be configured to be visualized fluoroscopically to aid identification of electrode locations relative to the cinch device. Accordingly, a position of the ablation device (15) relative to the cinch device may be verified. In some embodiments, the signal generator may be configured to deliver a voltage only to the subset of electrodes that are uncovered by the cinch device to deliver ablation energy to tissue.

In some embodiments, the voltage generator setting for irreversible electroporation may be automatically identified by the electroporation system based on this distance measure corresponding to electrode location. In some embodiments, the voltage value may be selected directly by a user from a suitable dial, slider, touch screen, or any other user interface. The voltage pulse may result in a current flowing between the anode and cathode electrodes on opposite sides of the contour defined by the conjoint shapes of the two devices, with current flowing through the cardiac wall tissue and through the intervening blood in the cardiac chamber, with the current entering the cardiac tissue from the anode electrodes and returning back through the cathode electrodes. The forward and return current paths (leads) may be respectively disposed inside distinct devices and/or the same device. In some embodiments, all active electrodes on a given device may be of like polarity. Alternatively, in other embodiments, electrodes on a single device can be activated as anode-cathode sets. Areas of cardiac wall tissue where the electric field is sufficiently large for irreversible electroporation may be ablated during the voltage pulse application.

In some embodiments, the pulse waveform may be generated in synchronization with a pacing signal of the heart to avoid disruption of the sinus rhythm of the heart. In some embodiments, the electrodes may be configured in anode-cathode (e.g., bipole) subsets. The pulse waveform may include hierarchical waveforms to aid in tissue ablation and reduce damage to healthy tissue, as described in International Application Serial No. PCT/US2016/057664, as incorporated by reference herein.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Pulse waveforms for electroporation energy delivery as disclosed herein may enhance the safety, efficiency, and effectiveness of energy delivery to tissue by reducing the electric field threshold associated with irreversible electroporation, thus yielding more effective ablative lesions with a reduction in total energy delivered.

The methods described here may include placing tissue (e.g., pulmonary vein) in contact with the electrodes. A pulse waveform may be generated and delivered to one or more electrodes of the device to ablate tissue. In some embodiments, the pulse waveform may be generated in synchronization with a pacing signal of the heart to avoid disruption of the sinus rhythm of the heart. In some embodiments, the electrodes may be configured in anode-cathode (e.g., bipole) subsets. The pulse waveform may include hierarchical waveforms to aid in tissue ablation and reduce damage to healthy tissue.

I. Systems

Overview

Disclosed herein are systems and devices configured for tissue ablation via the selective and rapid application of voltage pulse waveforms to aid tissue ablation, resulting in irreversible electroporation. Generally, a system for ablating tissue described here may include a signal generator and an ablation device having one or more electrodes for the selective and rapid application of DC voltage to drive electroporation. As described in more detail herein, the systems and devices described herein include one or more ablation devices configured to ablate tissue of the heart. Voltages may be applied to a selected subset of the electrodes, with independent subset selections for anode and cathode electrode selections. The ablation device may be coupled to one or more electrode channels of the signal generator. Each electrode channel, or subset of electrode channels, may be independently configured as an anode or cathode and a voltage pulse waveform may be delivered through one or more of the electrode channels in a predetermined sequence. A pacing signal for cardiac stimulation may be generated and used to generate the pulse waveform by the signal generator in synchronization with the pacing signal.

Figure 8:
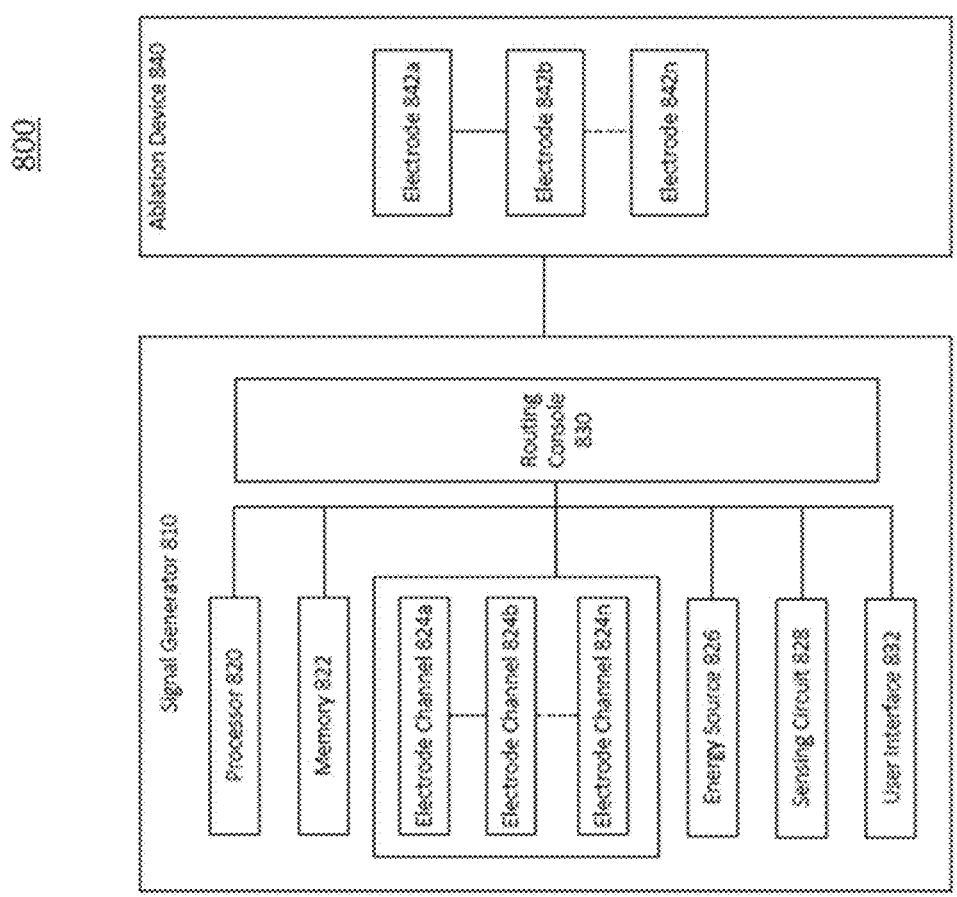
FIG. 8 is a block diagram of an electroporation system, according to embodiments.

FIG. 8 schematically illustrates an ablation system (800) configured to deliver voltage pulse waveforms for tissue ablation. The system (800) may include a signal generator (810) and ablation device (840). The signal generator (810) may be coupled to at least one ablation device (840) having a set of one or more electrodes (842a, 842b, . . . , 842n).

Signal Generator

The signal generator (810) may be configured to generate pulse waveforms for irreversible electroporation of tissue, such as, for example, heart tissue. The signal generator (810) may be a voltage pulse waveform generator and deliver a pulse waveform to a set of electrodes (842a, 842b, . . . , 842n) of the ablation device (840). The signal generator (810) may generate and deliver several types of signals including, but not limited to, radiofrequency (RF), direct current (DC) impulses (such as high-voltage, ultra-short pulses used in electroporation), stimulus range impulses, and/or hybrid electrical impulses. For example, the signal generator (810) may generate monophasic (DC) pulses and biphasic (DC and AC) pulses. The signal generator (810) may include a processor (820), memory (822), a set of electrode channels (824a, 824b, . . . , 824n), energy source (826), sensing circuit (828), routing console (830), and user interface (832). One or more signal generator components may be coupled using a communication bus. The processor (820) may incorporate data received from one or more of memory (822), electrode channels (824a, 824b, . . . , 824n), energy source (826), sensing circuit (828), routing console (830), user interface (832), ablation device (840) to determine the parameters (e.g., amplitude, width, duty cycle, timing, etc.) of the voltage pulse waveform to be generated by the signal generator (810). The memory (822) may further store instructions to cause the processor (820) to execute modules, processes and/or functions associated with the system (800), such as pulse waveform generation and delivery, and/or electrode channel configuration. For example, the memory (822) may be configured to store anode/cathode configuration data, electrode channel configuration data, pulse waveform data, fault data, energy discharge data, heart pacing data, patient data, clinical data, procedure data, sensor data, temperature data, and/or the like.

In some embodiments, the ablation device (840) (similar to any of the devices illustrated in FIGS. 1-4, 6, 7, 14, and 15) may include a device configured to receive and/or deliver the pulse waveforms described herein. For example, the ablation device (840) may be introduced around a pulmonary vein and positioned to align one or more electrodes (842a, 842b, . . . , 842n) to heart tissue, and then deliver the pulse waveforms to ablate tissue. The ablation device (840) may include one or more electrodes (842a, 842b, . . . , 842n), which may, in some embodiments, be a set of independently addressable electrodes. For example, the electrodes (842a, 842b, . . . , 842n) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like. The set of electrodes (842a, 842b, . . . , 842n) may include any number of electrodes, for example, 2, 3, 4, 5, 6, 7, 8, 9, 10, 12, or more electrodes. In some embodiments, predetermined subsets of electrodes may be electrically wired together so that each such subset is independently addressable. In some embodiments, the methods, systems, and devices disclosed herein may include one or more of the methods, systems, and devices described in U.S. patent application Ser. No. 15/499,804, filed on Apr. 27, 2017, and titled "SYSTEMS, DEVICES, AND METHODS FOR SIGNAL GENERATION"; International Application Serial No. PCT/US17/12099, filed on Jan. 4, 2017, and titled "SYSTEMS, DEVICES, AND METHODS FOR DELIVERY OF PULSED ELECTRIC FIELD ABLATIVE ENERGY TO ENDOCARDIAL TISSUE"; International Application Serial No. PCT/US2013/031252, filed on Mar. 14, 2013, and titled "CATHETERS, CATHETER SYSTEMS, AND METHODS FOR PUNCTURING THROUGH A TISSUE STRUCTURE AND ABLATING A TIS SUE REGION"; International Application Serial No. PCT/US2018/029552, filed on Apr. 26, 2018, and titled "SYSTEMS, DEVICES, AND METHODS FOR SIGNAL GENERATION"; and International Application Serial No. PCT/US2019/014226, filed on Jan. 18, 2019, and titled "SYSTEMS, DEVICES, AND METHODS FOR FOCAL ABLATION", the contents of each of which are hereby incorporated by reference in their entirety.

In some embodiments, the processor (820) may be any suitable processing device configured to run and/or execute a set of instructions or code and may include one or more data processors, image processors, graphics processing units, physics processing units, digital signal processors, and/or central processing units. The processor (820) may be, for example, a general purpose processor, Field Programmable Gate Array (FPGA), an Application Specific Integrated Circuit (ASIC), and/or the like. The processor (820) may be configured to run and/or execute application processes and/or other modules, processes and/or functions associated with the system and/or a network associated therewith (not shown). In some embodiments, the processor may include both a microcontroller unit and an FPGA unit, with the microcontroller sending electrode sequence instructions to the FPGA. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

In some embodiments, the memory (822) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory (822) may store instructions to cause the processor (820) to execute modules, processes and/or functions associated with the system (800), such as pulse waveform generation and/or electrode channel configuration.

In some embodiments, a set of electrode channels (824a, 824b, . . . , 824n) may include a set of active solid-state switches. The set of electrode channels (824a, 824b, . . . , 824n) may be configured in a number of ways, including independent anode/cathode configuration for each electrode channel. For example, the electrode channels (824a, 824b, . . . , 824n) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like. The set of electrode channels (824a, 824b, . . . , 824n) may include any number of channels, for example, 2, 3, 4, 5, 6, 7, 8, 9, 10, 12, or more electrode channels. Energy delivery may use any combination of electrode channels (824a, 824b, . . . , 824n) and any order for an energy delivery sequence. The energy delivered may be an RF and/or any tissue ablation energy.

The set of electrode channels (824a, 824b, . . . , 824n) may be coupled to a routing console (830) to deliver energy to a set of electrodes (842) coupled to the routing console (830). The set of electrode channels (824a, 824b, . . . , 824n) may be coupled to an energy source (826) to receive energy (e.g., a pulse waveform). Processor (820) may be coupled to each electrode channel (824a, 824b, . . . , 824n) to configure an anode/cathode configuration for each electrode channel (824), which may be configured on a per pulse basis, per operator input, and/or the like. In some embodiments, each electrode channel (824a, 824b, . . . , 824n) may include an electronic switch (e.g., bipolar transistor) and a drive circuit, as described in detail herein. In some embodiments, each electrode channel (824a, 824b, . . . , 824n) may have a bootstrap configuration for low and high frequency operation. For example, the pulse duration of voltage pulses delivered through an electrode channel may be in the range of between about 1 microsecond and about 1000 microseconds. In biphasic mode, this corresponds to an approximate frequency range of between about 500 Hz and about 500 KHz for the frequency associated with the voltage pulses.

In some embodiments, a controller including the processor (820) and memory (822) may be coupled to each electrode of the set of electrodes (842). The controller may be configured to generate a pulse waveform and configure the set of electrodes (842) for pulse waveform delivery. The pulse waveform may be delivered to the set of electrodes (842).

In some embodiments, an energy source (826) may be configured to convert and supply energy to a set of electrodes (842) coupled to the signal generator (810). The energy source (826) of the signal generator (810) may include a DC power supply and be configured as an AC/DC switcher. In some embodiments, an energy source (826) of the signal generator (810) may deliver rectangular-wave pulses with a peak maximum voltage of up to about 7 kV into a device with an impedance in the range of between about 30Ω and about 3000Ω with a pulse width in the range between about 1 microsecond and about 500 microseconds, including all values and subranges in between. In some of these embodiments, the energy source (826) may be configured to store energy. For example, the energy source (826) may include one or more capacitors to store energy from a power supply. While these examples are included for purely non-limiting illustrative purposes, it is noted that a variety of pulse waveforms with a range of pulse durations, intervals between pulses, pulse groupings, etc. may be generated depending on the clinical application.

In some embodiments, a sensing circuit (828) may be configured to determine an amount of current being delivered to a device coupled to the signal generator (810) (e.g., electrode (842) coupled to the electrode channel (824)). As described in more detail herein, the sensing circuit (828) may also be used to classify an electrode channel fault, monitor capacitor discharge, and/or sense arcing. In some embodiments, the sensing circuit (828) may be a direct current sensing circuit and/or a low-side sensing circuit. The sensing circuit may include one or more operational amplifiers, difference amplifiers (DA), instrumentation amplifiers (IA), and/or current shunt monitors (CSM).

In some embodiments, the routing console (830) may be configured to electrically couple a set of electrodes (842) of an ablation device (840) to a set of electrode channels (824a, 824b, . . . , 824n). The routing console (830) may be configured to selectively deliver energy to the set of electrodes (842) using the set of electrode channels (824a, 824b, . . . , 824n). One or more ablation devices (840) each having a set of electrodes (842) may be coupled to the routing console (830). The set of electrodes (842) may include any number of electrodes, for example, 1, 2, 3, 4, 5, 6, 7, 8, 9, 10, 12, or more electrodes.

In some embodiments, the electrode channels (824a, 824b, . . . , 824n) configured for energy delivery (e.g., configured as an anode/cathode pair of electrode channels)

may not be adjacent to each other but may be arbitrarily disposed along the ablation device (840).

A multi-electrode ablation device may allow targeted and precise energy delivery to tissue. In some embodiments, the electrodes (842) of an ablation device (840) may be configured for energy delivery (e.g., as an anode/cathode pair of electrodes (842) and may be disposed on adjacent or any other relative locations along the ablation device (840). The signal generator (810) coupled to the ablation device (840) may include a set of electrode channels (824a, 824b, ..., 824n) having N electrode channels corresponding to M electrodes (842n) of the ablation device (840). Each electrode channel (824a, 824b, ..., 824n) of the signal generator (810) may be coupled to one of the electrodes (842) of the ablation device (840).

Configurable electrode channel and electrode selection may provide flexibility in positioning the electrodes for ablating a desired region of interest, as described in more detail herein. The routing console (830) may receive input from the processor (820) and/or user interface (832) for electrode channel selection and energy delivery to one or more electrodes (842).

In some embodiments, a user interface (832) may be configured as a communication interface between an operator and the system (800). The user interface (832) may include an input device and output device (e.g., touch surface and display). For example, patient data from memory (822) may be received by user interface (832) and output visually and/or audibly. Electric current data from sensing circuit (828) may be received and output on a display of user interface (832). As another example, operator control of an input device having one or more buttons, knobs, dials, switches, trackball, touch surface, and/or the like, may generate a control signal to the signal generator (810) and/or ablation device (840).

In some embodiments, an input device of the user interface (832) may include a touch surface for operator input and may be configured to detect contact and movement on the touch surface using any of a plurality of touch sensitivity technologies including capacitive, resistive, infrared, optical imaging, dispersive signal, acoustic pulse recognition, and surface acoustic wave technologies. Additionally or alternatively, the user interface (832) may include a step switch or foot pedal.

In some embodiments, an output device of the user interface (832) may include one or more of a display device and audio device. The display device may include at least one of a light emitting diode (LED), liquid crystal display (LCD), electroluminescent display (ELD), plasma display panel (PDP), thin film transistor (TFT), and organic light emitting diodes (OLED). An audio device may audibly output patient data, sensor data, system data, other data, alarms, warnings, and/or the like. The audio device may include at least one of a speaker, piezoelectric audio device, magnetostrictive speaker, and/or digital speaker. In one embodiment, the audio device may output an audible warning upon detection of a fault in the signal generator (810) and/or ablation device (840).

In some embodiments, the signal generator (810) may be mounted on a trolley or cart. In some embodiments, the user interface (832) may be formed in the same or different housing as the signal generator (810). The user interface (832) may be mounted to any suitable object, such as furniture (e.g., a bed rail), a wall, a ceiling, or may be self-standing. In some embodiments, the input device may include a wired and/or wireless transmitter configured to transmit a control signal to a wired and/or wireless receiver of the signal generator (810).

In some embodiments, the systems described herein may include one or more sterile coverings configured to create a sterile barrier around portions of the system (800). In some embodiments, the system (800) may include one or more sterile coverings to form a sterile field. For example, a sterile covering may be placed between the ablation device(s) and the patient, forming a barrier between an interior, non-sterile side including the patient, signal generator, and ablation devices and an exterior, sterile side including the operator. Additionally or alternatively, components of the system (800) may be sterilizable. The sterile covering may include, for example, a sterile drape configured to cover at least a portion of a system component. In one embodiment, a sterile covering (e.g., sterile drape) may be configured to create a sterile barrier with respect to a user interface (832) of the system (800). The sterile drape may be clear and allow an operator to visualize and manually manipulate the user interface (832). The sterile covering may conform tightly around one or more system components or may drape loosely so as to allow components to be adjusted within the sterile field.

Ablation Device and Cinch Device

The systems described here may include one or more multi-electrode ablation devices (e.g., catheters) configured to ablate tissue for treating a heart condition and a cinch device configured to aid in positioning of the ablation device relative to the tissue. In some embodiments, the ablation device may be configured to be positioned against tissue using a cinch device. The cinch device may include an elongate shaft defining a pair of parallel lumens. In some embodiments, a distal end of the elongate shaft may be curved to aid introduction of the ablation device into a pericardial space. In some embodiments, the cinch device may include a set of fiducials configured for visualization (e.g., imaging by fluoroscopy, X-ray). An ablation device and cinch device may be configured for use in a cardiac procedure, such as, for example, creation of a box lesion around the pulmonary veins in the epicardial or pericardial space.

Generally, the ablation devices may include a set of metallic electrodes. The electrodes may also be generally atraumatic so as to decrease the risk of damage to tissue through laceration and puncture. For example, the edges of the electrodes may be rounded to reduce tissue damage and to increase the uniformity of the electric field generated at a central portion and a peripheral portion of the electrodes. In order to deliver the pulse waveforms generated by the signal generator, one or more electrodes of the ablation device may have an insulated electrical lead configured for sustaining a voltage potential of at least about 700 V without dielectric breakdown of its corresponding insulation. In some embodiments, the insulation on each of the electrical leads may sustain an electrical potential difference of between about 200 V and about 3,000 V across its thickness without dielectric breakdown, including all values and sub-ranges in between. The electrodes may be independently addressable such that each electrode may be controlled (e.g., deliver energy) independently of any other electrode of the ablation device. The electrodes may, for example, be connected to an insulated electrical lead coupled to a signal generator to receive pulse waveforms as described herein.

FIG. 1 is a perspective view of an ablation device (102) and cinch device (130). Generally, the cinch device (130) may have a double-barrel configuration sized to allow the ablation device to pass through it. For example, the ablation device (102) may be looped around a set of pulmonary veins (not shown in FIG. 1) and through the cinch device (130) such that the proximal and distal ends of the ablation device (102) may be disposed outside the body and generally adjacent to each other. That is, the ends of the ablation device (102) may be disposed proximal to the cinch device (130). The cinch device (130) may then be manipulated to tighten the loop formed by the ablation device (102) around the pulmonary veins to aid positioning of the ablation device for tissue ablation. The ablation device (102) may include a handle (104) coupled to a proximal portion of the ablation device (102) and a distal tip (101). The distal tip (101) may include an atraumatic shape to reduce trauma to tissue. The ablation device (102) may be configured to be slidably disposed within a first lumen (106) and a second lumen (131) of the cinch device (130). The first and second lumens (106, 131) may correspond to respective hollow tubular structures (e.g., first cinch catheter, second cinch catheter) that may be joined together along their length (L) to form a double-barreled or double lumen structure. The cinch device (130) may define a longitudinal axis.

In some embodiments, the ablation device (102) can include a series of fiducials or markings at its proximal and distal ends. For example, a series of markings (112, 114) can be disposed on a distal section of the ablation device (102), and a series of markings (144, 146) can be disposed on a proximal section of the ablation device (102). As explained in further detail in reference to later figures, these series of markings can be used to determine the electrodes (e.g., electrodes (108)) that are disposed inside or outside of the cinch device (130), as described in further detail with reference to FIGS. 2-5. For example, the spacing between markings (112, 114) can be set to correspond to a length of a group of electrodes and/or a distance between groups of electrodes. In some embodiments, the length (L) of the cinch device (130) can be a multiple of such length and/or distance, to further facilitate determination of a number of electrodes or groups of electrodes inside or outside of the cinch device (130).

In some embodiments, the cinch device (130) may be sized and shaped for subxiphoid access. For example, the cinch device (130) may include a curved distal portion, as described herein with respect to FIGS. 9A-9D. The ablation device (102) may have a diameter smaller than a diameter of the cinch device (130). In some embodiments, during use, the ablation device (102) may be introduced into a proximal end of first lumen (106) of the cinch device (130). The ablation device (102) may extend from a distal end of the first lumen (106) and be configured to form a loop. For example, the ablation device (102) may include a central portion (124) having high flexibility (e.g., a flexible curvature). The ablation device (102) may then be introduced into a distal end of second lumen (131). The ablation device (102) may extend from a proximal end of the second lumen (131) such that the distal tip (101) of the ablation device (102) may be advanced out of the proximal end of the second lumen (131). The cinch device (130) may be sized to ensure that a suitable number of the electrodes (108) on the ablation device (102) may be drawn or pulled into each lumen (106, 131) of the cinch device (130). Further, a desired length of the ablation device (102) may extend from a proximal end of the cinch device (130) for manipulation when the ablation device (102) forms a loop and is advanced through the cinch device (130). For example, the cinch device (130) may have a length in the range between about 6 cm and about 30 cm, including all values and sub-ranges in-between. A distal portion of the ablation device (e.g., distal to the electrodes (108)) may have a length in the range between about 20 cm and about 70 cm, including all values and sub-ranges in-between.

The ablation device (102) may include one or more electrodes (108) formed on a surface of the ablation device (102). In FIG. 1, a set of electrodes (108) are disposed along a central portion (124) of the ablation device (102). In some embodiments, each electrode (108) may be independently addressable, while in other embodiments one or more subsets of electrodes (108) may be electrically wired together. For example, a set of three or four adjacent electrodes may be electrically wired together as an electrode subset. In some embodiments, non-adjacent electrodes may be electrically wired together. In some embodiments, a spacing between successive electrodes and/or electrode subsets may vary. Each electrode (108) may include or be attached to an insulated electrical lead configured to sustain a voltage potential of at least about 700 V without dielectric breakdown of its corresponding insulation. In cases where more than one electrode is electrically wired together as an electrode group, a single such insulated lead may be connected to the electrode group. In some embodiments, the electrodes (108) may have about the same size, shape, and/or spacing. In some embodiments, the size, shape, and spacing of the electrodes (108) may differ.

The ablation device (102) may be configured for delivering a set of voltage pulse waveforms using a set of electrodes (108) to ablate tissue and electrically isolate one or more regions of the heart. At least a portion of the ablation device (102) may include a flexible curvature. For example, a central portion (124) of the ablation device (102) disposed between a proximal portion and a distal portion of the ablation device (102) may be flexible and configured to conform to a cardiac anatomy. The ablation device (102) may be configured to transform between a first configuration where the ablation device (102) is partially advanced into the cinch device (130) and a second configuration where the central portion (124) of the ablation device (102) forms a loop that may be configured to encircle tissue such as a pulmonary vein firmly. In this manner, the ablation device (102) and cinch device (130) may increase contact with heart tissue.

In some of these embodiments, a handle (104) may be coupled to the ablation device (102) to form a hub from which an electrical cable and/or connector (not shown) may be attached and for providing an entry point for guidewire introduction. The connector may connect directly or through an extension cable to a signal generator for delivery of voltage waveforms for pulsed electric field ablation. In some embodiments, the handle (104) may include a guidewire lumen hub (not shown) for introduction of a guidewire that may provide mechanical support to the ablation device (102) when wrapped around tissue such as the pulmonary veins. In some embodiments, the handle may define a flush port configured for flushing a guidewire lumen to aid introduction of a guidewire.

In some embodiments, the cinch device (130) may be positioned within the pericardial space at a location that allows access to the pulmonary veins for an ablation device (102) such as described herein. The ablation device (102) may be advanced through a first lumen (106) and looped around a set of pulmonary veins (e.g., four pulmonary veins). For example, pericardial reflections or folds in the pericardial membrane may be excised to allow the ablation device (102) to encircle all four pulmonary veins at the base of the trunk of the veins. The ablation device (102) may be advanced through the second lumen (131). The cinch device (130) may be advanced towards the heart, angled obliquely relative to the patient's chest, and placed on a posterior side of the heart. The proximal and distal ends of the ablation device (102) may be drawn through the cinch device (130) and pulled away from the heart to apply a predetermined amount of force to the pulmonary veins using the looped central portion (124) of the ablation device (102).

The number of electrodes that may be drawn into the cinch device (130) when the ablation device (102) is tightened around the pulmonary veins may depend on the size of the left atrium and the amount of force applied. Any electrodes (108) disposed within a lumen of the cinch device (130) should not receive energy while the electrodes (108) looped around and in contact with the pulmonary veins. Electrodes (108) distal to a distal end of the cinch device (130) may be configured to receive ablation energy. Some embodiments described herein may provide a direct visual means to identify a location of a set of electrodes (108) of an ablation device (102) relative to the cinch device (130).

Figure 6A:
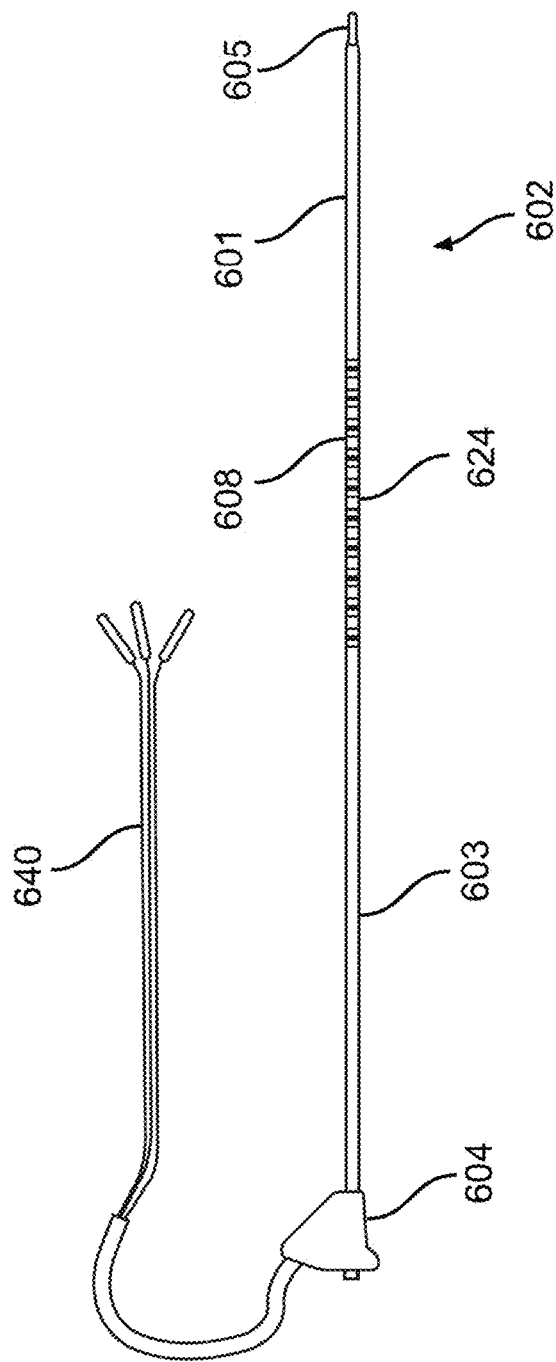
FIG. 6A is a side view of an ablation device, according to embodiments.
Figure 6C:
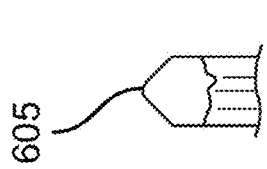
FIG. 6C is a perspective view of a distal tip of the ablation device of FIG. 6A.
Figure 6B:
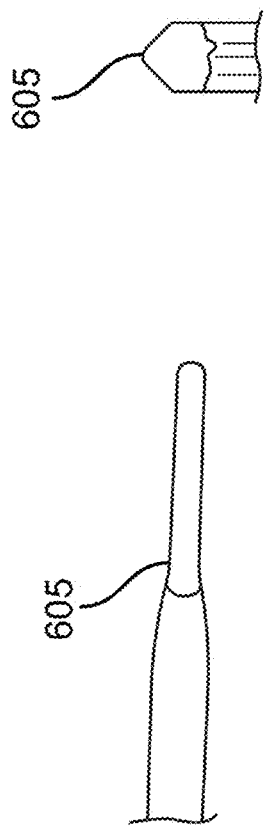
FIG. 6B is a perspective view of a distal portion of the ablation device of FIG. 6A.

FIG. 6A is a side view of an example, non-limiting ablation device (602). The ablation device (602) may include a catheter having a proximal portion (603), a central portion (624), and a distal portion (601). The proximal, distal, and central portions of the may each be composed of a compliant and/or flexible material to allow one or more portions of the ablation device (602) to easily conform to a cardiac anatomy. The distal portion (601) may include an atraumatic distal tip (605) such as shown in FIGS. 6B and 6C. The central portion (624) may include a set of electrodes (608) disposed on a surface of the ablation device (602). The set of electrodes (608) may include a plurality of subsets with each subset having a first length. Each subset of electrodes may be spaced apart from an adjacent subset by a second length. The second length may be greater than the first length. FIG. 6A shows the set of electrodes grouped into subsets of three electrodes each. Each electrode within a subset can have a third length. In some embodiments, one or more electrodes within a subset may have different lengths. For example, FIGS. 7A and 7B, described below, provide a more detailed view of subsets of three electrodes with varying lengths. Alternatively, each electrode within a subset may have the same length.

A handle (604) may be coupled to the proximal portion (603) of the ablation device (602). A set of lead wires (640) may be coupled to the handle (604) and may be disposed within a lumen of the ablation device (602) to connect to the set of electrodes (608).

Figure 7A:
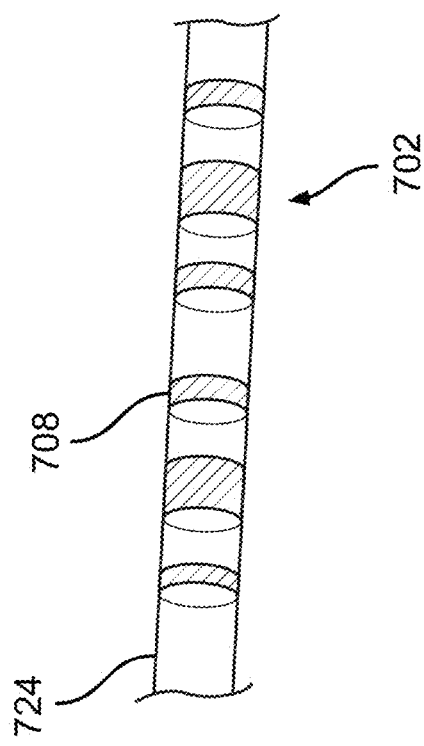
FIG. 7A is a side view of an ablation device including a set of electrodes, according to embodiments.
Figure 7B:
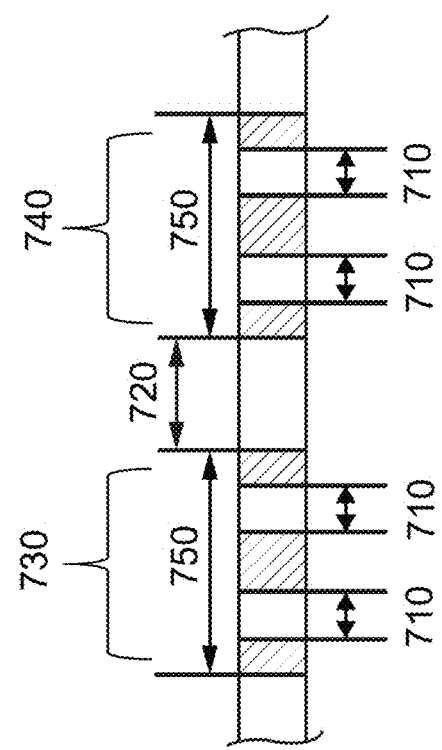
FIG. 7B is a side view of the set of electrodes of FIG. 7A with leads coupled thereto and disposed in the ablation device.

FIGS. 7A and 7B are side views of a set of electrodes (708) of an example ablation device (702). The set of electrodes (708) may be disposed on a central portion (724) of the ablation device (702). As described herein, one or more sets of the electrodes (708) may not be used to deliver ablation energy such as when those electrodes are disposed within a lumen of a cinch device. The electrode subsets (730, 740) may have a first length (750) and may be separated by a second length (720). In some embodiments, the electrodes may be formed of platinum-iridium material. In some embodiments, the set of electrodes (708) may include a multiplicity of triplet subsets or groups where the electrodes (each in the form of rings) may have a third length in the range between about 1 mm and about 12 mm, including all values and sub-ranges in-between. Each electrode within a subset or group of electrodes (730, 740) may be separated by a fourth length (710). In some embodiments, the number of electrode subsets may range between about 4 and about 20, including all values and sub-ranges in-between.

Figure 9:
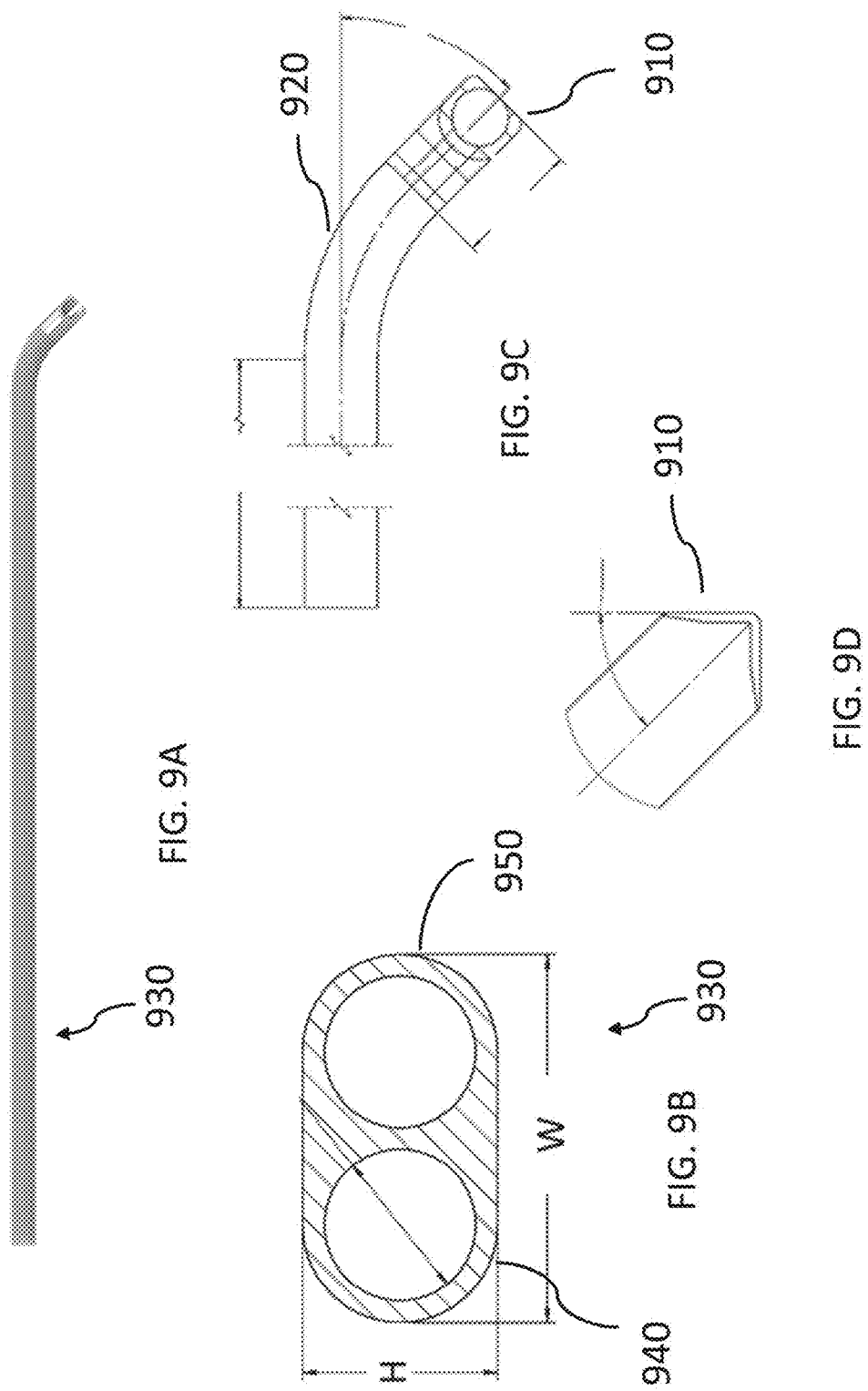
FIG. 9A is a side view of a cinch device, according to embodiments.
FIG. 9B is a schematic cross-sectional side view of the cinch device of FIG. 9A.
FIG. 9C is a schematic side view of a distal end of the cinch device of FIG. 9A.
FIG. 9D is a schematic side view of a distal tip of the cinch device of FIG. 9A.

FIG. 9A is a side view of a cinch device (930). The cinch device may include a distal portion having a curved portion (920) and a distal tip (910). The curved portion (920) may aid in positioning and advancement of an ablation device within a body cavity. FIG. 9B is a cross-sectional side view of a cinch device (930) having a first lumen (940) and a second lumen (950). The lumens (940, 950) may have the same diameter. The diameter can be about a diameter of an ablation catheter (not depicted) or larger such that it is designed for use therewith. FIGS. 9C and 9D are schematic side views of a distal end of a cinch device (930) including the curved portion (920) and distal tip (910). In some embodiments, the cinch device (930) may be formed of Pebax (e.g., Pebax 40D). In some embodiments, the distal tip (910) may have a length of between about 5 mm and about 25 mm, and may be composed of a material visible under fluoroscopy. In some embodiments, the one or more portions of the cinch device (930) (e.g., the entire surface of the cinch device (930)) may be visible under fluoroscopy. The distal tip (910) may be atraumatic to reduce trauma to tissue. In some embodiments, the curved portion (920) may have a curvature of between about 30 degrees and 60 degrees. For example, the curved portion (920) may have a curvature of about 45 degree.

Fiducials

In some embodiments, one or more of an ablation device and cinch device may include a set of fiducials that allow a surgeon and/or imaging system to determine a location of a set of electrodes of the ablation device relative to the cinch device. For example, a set of markings disposed on one or more of a proximal portion and distal portion of the ablation device may correspond to the number of electrodes or electrode subsets within a lumen (e.g., inside) of the cinch device and/or the number of electrodes or electrode sets disposed outside of the cinch device. Accordingly, the electrodes or electrode subsets within the cinch device may be configured to be deactivated while the remaining electrodes or electrode sets that extend or that are exposed outside of the cinch device may be configured to deliver ablation energy to tissue such as a portion around a set of pulmonary veins of the heart. As used herein, a fiducial corresponds to a mark, symbol (e.g., number, letter), geometric shape, hole, recession, protrusion, texture, combinations thereof, and the like disposed along a length of one or more of an ablation device and cinch device.

Figure 2:
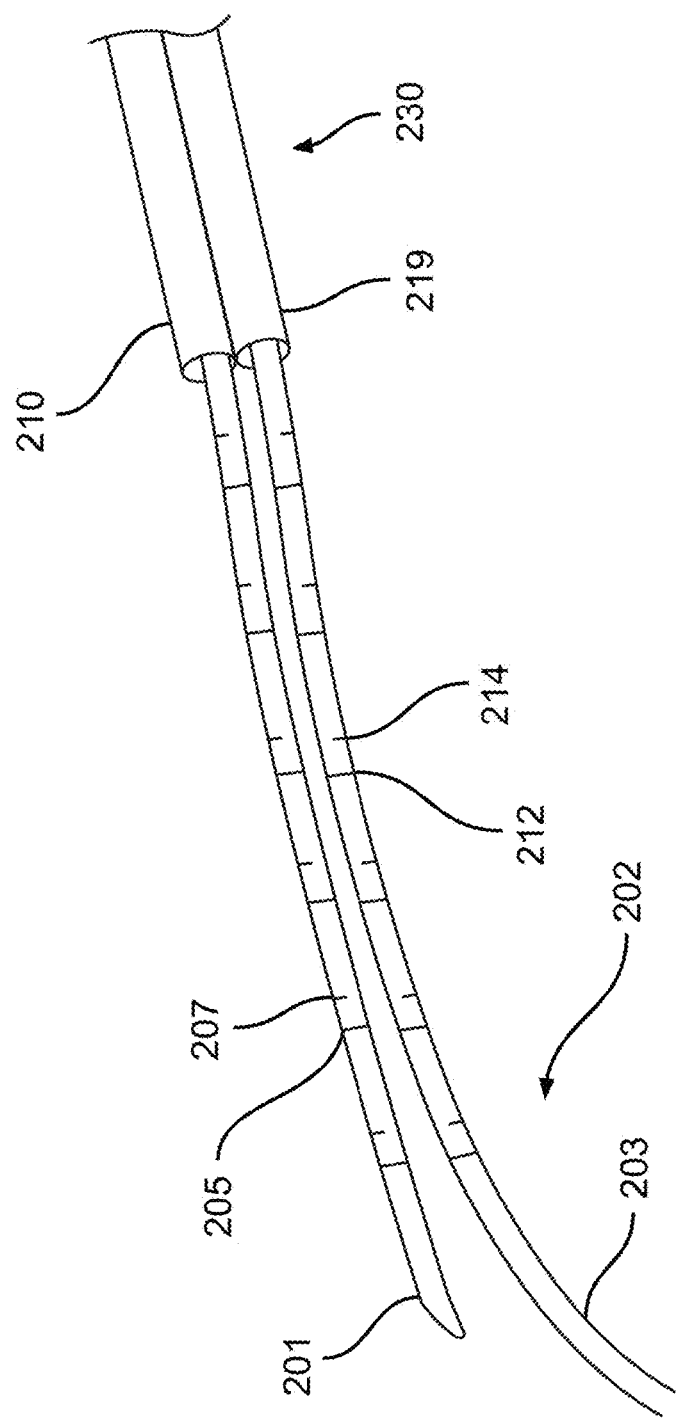
FIG. 2 is a perspective view of an ablation device and a cinch device including a portion of the ablation device protruding from the cinch device, according to embodiments.

FIG. 2 is a perspective view of an ablation device (202) and cinch device (230) where a proximal portion (203) of the ablation device (202) may be extended through a proximal end of a first lumen (219) of the cinch device (230). A distal portion (201) of the ablation device (202) may be extended through a proximal end of a second lumen (210) of the cinch device (230). The proximal portion (203) may include on its surface a first set of proximal fiducials (212) and a second set of proximal fiducials (214) disposed along its length. The first set of proximal fiducials (212) may be different (e.g., larger, wider) than the second set of proximal fiducials (214). Fiducials of the first and second set of proximal fiducials (212, 214) may be alternately disposed along a length of the ablation device (202). Adjacent fiducials of the first and second set of proximal fiducials (212, 214) may be spaced apart by a length of an electrode of the ablation device (202) (not shown in FIG. 2). Likewise, the distal portion (201) may include on its surface a first set of distal fiducials (205) and a second set of distal fiducials (207) disposed along its length. The first set of distal fiducials (205) may be larger than the second set of distal fiducials (207). Fiducials of the first and second set of distal fiducials (205, 207) may be alternately disposed along a length of the ablation device (202). Adjacent fiducials of the first and second set of distal fiducials (205, 207) may be spaced apart by a length of an electrode. In some embodiments, the first and second sets of fiducials (205, 207, 212, 214) may be identified and differentiated by number, location, length, thickness, width, depth, shape, color, orientation, texture, material, combinations thereof, and the like.

In some embodiments, each subset of electrodes of the ablation device (202) (e.g., a set of three adjacent electrodes electrically wired together) may have a first length, and the length of the cinch device (230) may be an integer multiple of the sum of the first length and the distance between successive electrode groups (second length). For example, if p denotes an end-to-end length of an electrode subset (first length) and d denotes a separation distance between electrode groups (second length), then the first set of fiducials (e.g., larger markings) may be disposed at a third length r=(p+d) away from the most distal and/or proximal electrode and repeat periodically at this length interval r (on both distal and proximal portions of the ablation device (202)). For example, the shorter markings may be adjacent to the larger markings with a spacing equal to a length of one electrode (e.g., length of the smallest electrode in each electrode subset, or a fifth length). The sets of fiducials disposed proximal to the cinch device (230) allow a surgeon to determine the number of electrodes disposed within the lumens of the cinch device (230) based on the number of sets of fiducials disposed proximal to the cinch device (230) (e.g., via visual confirmation, tactile confirmation, etc.). For example, if three complete sets (e.g., large and small) of fiducials disposed along the distal portion (201) of the ablation device (202) are visible proximal to the cinch device (230) such that the shorter markings of one set of fiducials are positioned at the proximal end of the cinch device (230), then two electrode subsets may be disposed within the second lumen (210) (e.g., depending on a length of the second lumen (210)), and the majority of electrodes of a third electrode subset may be disposed distal to the cinch device (230) and exposed for delivery of ablation energy. The number of electrode subsets disposed within the lumens of the cinch device (230) and the number of electrode subsets disposed distal to and exposed outside of the lumens of the cinch device (230) can depend on, for example, a length of the lumens of the cinch device (230), a total number of electrode subsets, etc.

Figure 15:
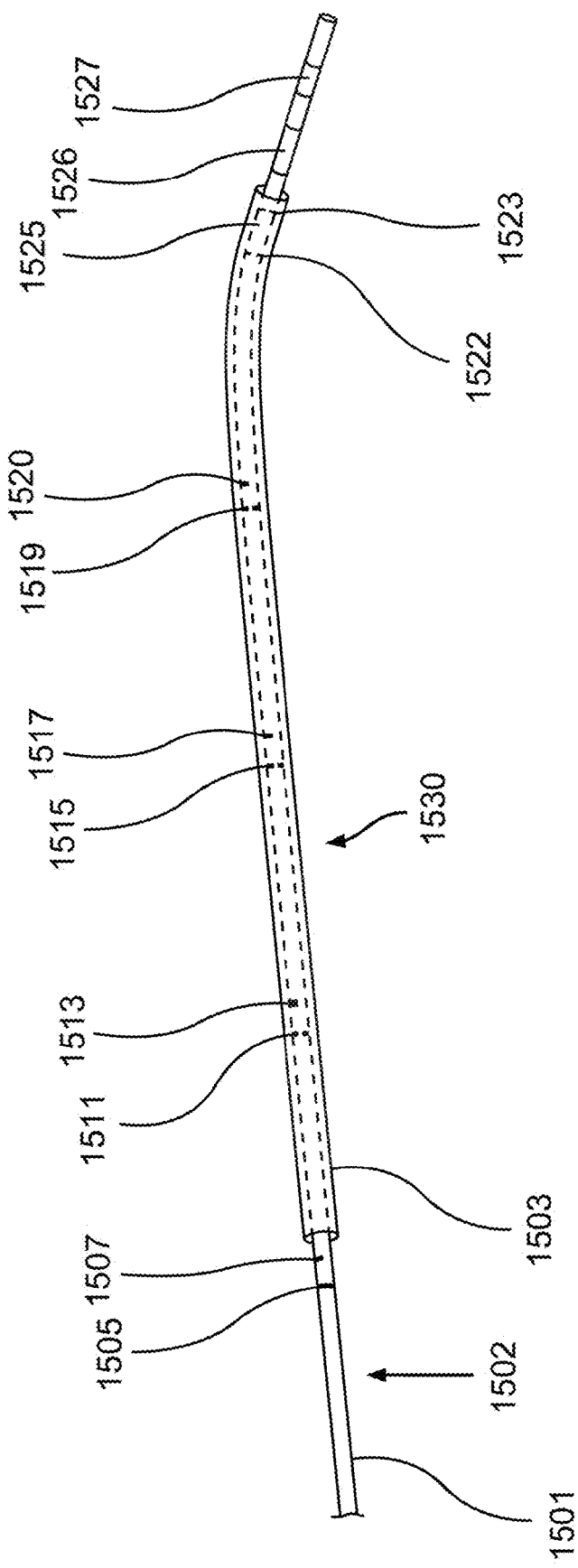
FIG. 15 is a perspective view of an ablation device and a cinch device including portions of the ablation device protruding from each end of the cinch device, according to embodiments.

For example, FIG. 15 depicts a distal portion (1501) of an ablation device (1502) in a lumen (1503) (e.g., lumen, barrel) of a cinch device (1530). For the sake of clarity, an adjoining lumen of the cinch device (1530) as well as a proximal portion of the ablation device (1502) is not shown. First and second sets of fiducials (1505, 1507, 1511, 1513, 1515, 1517, 1519, 1520) having longer and shorter markings respectively, are shown distributed along a distal portion (1501) of the ablation device (1502). While a pair of the fiducials (1505, 1507) are exposed and separated from a proximal end of the lumen (1503), the other three fiducial pairs (1511, 1513), (1515, 1517) and (1519, 1520) are disposed inside the lumen (1503).

A distal-most electrode subset of the ablation device (1502) may include a triplet of electrodes (1525, 1526, 1527). As depicted in FIG. 15, a distal end (1522) and a proximal end (1523) of the distal-most electrode (1525) of the triplet are disposed within the lumen (1503) such that electrodes (1526, 1527) are exposed and distal to the lumen (1503) and may be configured for ablation energy delivery.

In this embodiment, the length of the lumen (1503) may be four times the spacing between the distal ends of successive electrode triplets (e.g., sum of a first length and a second length). This spacing r, as described above, is the sum of the length p (first length) of an electrode triplet and the gap d (second length) between adjacent electrode triplets. The spacing between successive fiducial pairs (for example, the distance between larger fiducial (1511) and larger fiducial (1515)) may be configured as equal to the distance r between distal ends of successive electrode triplets. In this example, the lumen has a length that may be an integer multiple of the distance r (i.e., the distance between the distal ends of successive fiducials). Accordingly, the presence of fiducials (1505, 1507) exposed proximal to the lumen (1503) may visually confirm that a single electrode (in this example, the distal-most electrode (1525)) of the distal-most electrode triplet is disposed within the lumen (1503), while the rest of the electrodes (1526, 1527) of that electrode triplet are exposed distal to the lumen (1503).

It should be appreciated from the above description that various other fiducial configurations may enable other estimations. For example, in one embodiment, sets of fiducials may be used, with each fiducial set to replicate, represent, and/or otherwise correspond an electrode group (e.g., the electrode triplet in the above example). In some embodiments, the number of electrodes disposed within the lumen of a cinch device tube, as well as which electrodes of the most distal-most exposed electrode group are disposed within the lumen of the cinch device, may be visually confirmed, since a corresponding number of fiducial sets would be visible on the distal portion of the ablation proximal to the cinch device.

As another example, in another embodiment, a single fiducial may be separated successively by a length (e.g., distance r) corresponding to the distance between distal ends of successive electrode groups. The number of fiducials visible on the distal portion of an ablation device outside the cinch device may correspond to the number of electrode groups that are disposed within a lumen of the cinch device.

While an electrode group (e.g., subset of electrodes) in the form of an electrode triplet is illustrated and described with respect to FIG. 15, it should be apparent to one skilled in the art that other electrode groupings can be implemented. For example, electrode groups may be wired together in subsets of electrode duets, quartets, etc. without limitation, and the methods and implementations provided as examples herein may be altered in details without departing from the scope of the present invention. In some embodiments, each electrode within a group can have the same length (e.g., as depicted in FIG. 15), while in other embodiments, electrodes within a group can have different lengths (e.g., as depicted in FIGS. 7A and 7B).

Figure 3:
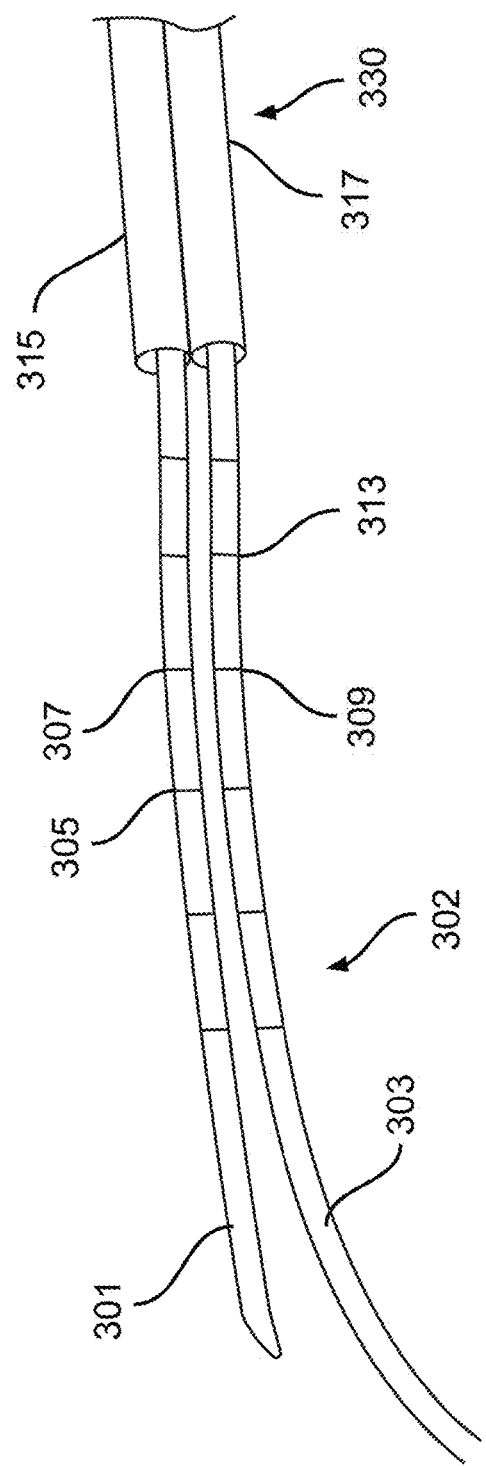
FIG. 3 is a perspective view of an ablation device and a cinch device including a portion of the ablation device protruding from the cinch device, according to embodiments.

FIG. 3 is a perspective view of an ablation device (302) and cinch device (330) where a proximal portion (303) of the ablation device (302) may be extended through a proximal end of a first lumen (317) of the cinch device (330). A distal portion (301) of the ablation device (302) may be extended through a proximal end of a second lumen (315) of the cinch device (330). The proximal portion (303) may include on its surface a set of proximal fiducials (309, 313) (e.g., markings) disposed along its length. The distal portion (301) may include on its surface a set of distal fiducials (305, 307) (e.g., markings) disposed along its length. In some embodiments, the proximal and distal set of fiducials may be identified and differentiated by one or more characteristics including number, location, length, thickness, width, depth, spacing, shape, color, pattern, orientation, texture, material, combinations thereof, and the like.

In some embodiments, each subset of electrodes of the ablation device (302) (e.g., a set of three adjacent electrodes electrically wired together) may have the same length, and the length of the cinch device (330) may be an integer multiple of the sum of the electrode subset length and the distance between successive electrode groups. For example, if p denotes an end-to-end length of an electrode subset and d denotes a separation distance between electrode groups, then the set of fiducials may be disposed starting at a distance r=(p+d) away from the distal-most and/or proximal electrode and repeat periodically at this length interval r, e.g., on both distal and proximal portions of the ablation device (302).

The set of fiducials disposed proximal to the cinch device (330) allow a surgeon to determine the number of electrodes disposed within the lumens of the cinch device (330) based on the number of fiducials disposed proximal to the cinch device (330) determined based on visual confirmation, tactile confirmation, and/or other types of confirmation. For example, if four complete fiducials disposed along the distal portion (301) of the ablation device (302) are visible outside the cinch device (330), then three electrode subsets may be disposed within the second lumen (315) of the cinch device (330). Depending on whether or not more than half of the length p is visible between the mark closest to the cinch device (330) and the proximal end of the cinch device (330), a fourth electrode group may be determined to be either inside the cinch device (330) or exposed outside the cinch device (330), respectively.

Furthermore, the number of electrode subsets disposed within the first lumen (317) of the cinch device (330) may be determined using the exposed fiducials (e.g., visual, tactile, etc.) disposed along the length of the proximal portion (303) of the ablation device (302) proximal to the cinch device (302). For example, two electrode subsets may be determined to be disposed within the first lumen (317) of the cinch device (330) based on the number of visible fiducials along the proximal portion (303). Once the number of electrode subsets in the first and second lumens (317, 315) are determined, a signal generator may be configured to deliver energy to electrodes that are looped around the pulmonary veins (and therefore exposed) without delivering energy to electrodes within the cinch device (330). For example, a user may enter fiducial information into a user interface of the signal generator.

Figure 4:
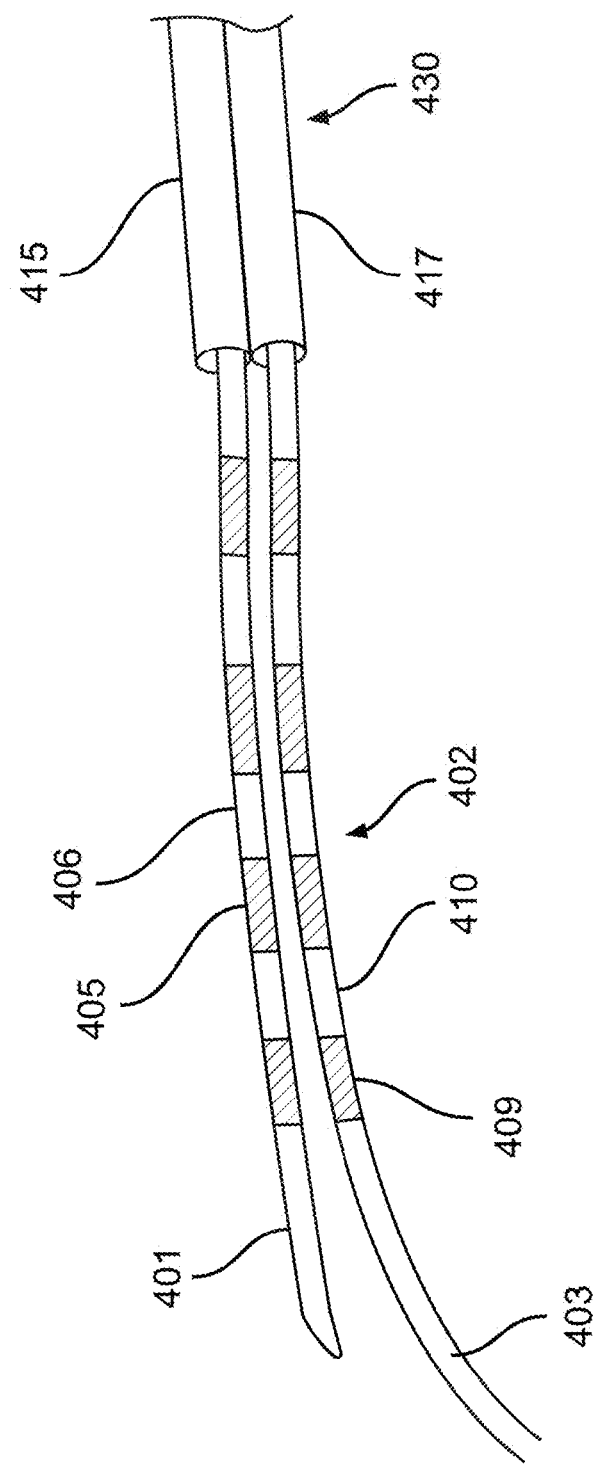
FIG. 4 is a perspective view of an ablation device and a cinch device including a portion of the ablation device protruding from the cinch device, according to embodiments.

FIG. 4 is a perspective view of an ablation device (402) and cinch device (430) where a proximal portion (403) of the ablation device (402) may be extended through a proximal end of a first lumen (417) of the cinch device (430). The ablation device (402) can be similar to other ablation devices described herein, but have fiducials implemented as alternating dark and light bands. A distal portion (401) of the ablation device (402) may be extended through a proximal end of a second lumen (415) of the cinch device (430). The proximal portion (403) may include on its surface a set of proximal fiducials (409, 410) (e.g., alternating dark and light bands) disposed along its length. The distal portion (401) may include on its surface a set of distal fiducials (405, 406) (e.g., alternating dark and light bands) disposed along its length. In some embodiments, the proximal and distal set of fiducials may be identified and differentiated by number, location, length, thickness, spacing, width, depth, shape, color, pattern, orientation, texture, combinations thereof, and the like.

In some embodiments, each subset of electrodes of the ablation device (402) (e.g., a set of three adjacent electrodes electrically wired together) may have the same length, and the length of the cinch device may be an integer multiple of the sum of the electrode subset length and the distance between successive electrode groups. For example, if p denotes an end-to-end length of an electrode subset and d denotes a separation distance between electrode groups, then the set of fiducials may be disposed in the form of alternating bands of length r=(p+d) starting from the distal-most electrode edge on the distal portion and starting from the proximal-most electrode edge on the proximal portion of the ablation device respectively.

The set of fiducials disposed outside the cinch device (430) allow a surgeon to determine the number of electrodes disposed within the lumens of the cinch device (430) based on the number of fiducials disposed outside the cinch device (430) that can be determined using visual, tactile, etc. confirmation. For example, if four complete sets of bands disposed along the distal portion (401) of the ablation device (402) are visible proximal to the cinch device (430), then at least three electrode subsets may be disposed within the second lumen (415) of the cinch device (430). Depending on whether or not more than half of the length p is visible between the mark closest to the cinch device (430) and the proximal end of the cinch device (430), a fourth electrode group may be determined to be either inside the cinch device (430) or exposed outside the cinch device (430), respectively.

Furthermore, the number of electrode subsets disposed within the first lumen (417) of the cinch device (430) may be determined using the visible fiducials disposed along the length of the proximal portion (403) of the ablation device (402) proximal to the cinch device (402). For example, two electrode subsets may be determined to be disposed within the first lumen (417) of the cinch device (430) based on the number of visible fiducials along the proximal portion (403). Once the number of electrode subsets in the first and second lumens (417, 415) are determined, a signal generator may be configured to deliver energy to the exposed electrodes looped around the pulmonary veins without delivering energy to electrodes within the cinch device (430). For example, a user may enter fiducial information into a user interface of the signal generator.

Figure 5:
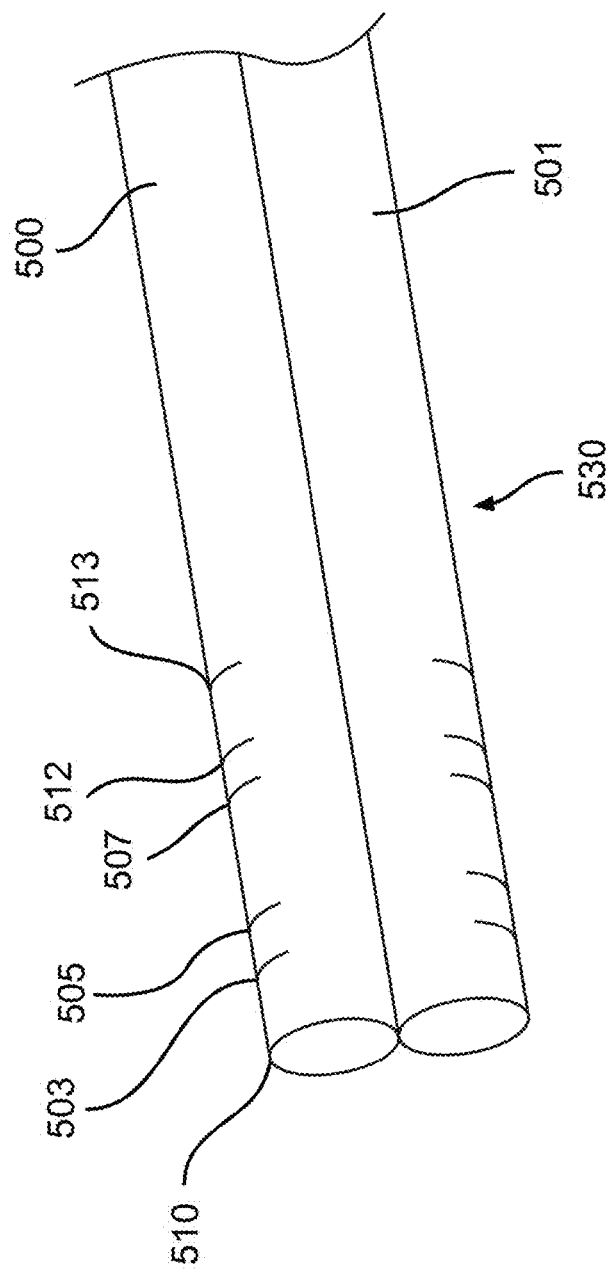
FIG. 5 is a perspective view of a cinch device including a set of fiducials on a portion of the cinch device, according to embodiments.

FIG. 5 is a perspective view of a cinch device (530) including a first lumen (501) (e.g., proximal tube) and a second lumen (500) (e.g., distal tube). The first and second lumens (501, 500) may include on its surface a set of fiducials (503, 505, 507, 512, 513) disposed along its length adjacent to a proximal end (510) of the cinch device (530). In some embodiments, the set of fiducials may be identified and differentiated by number, location, length, thickness, width, depth, shape, color, pattern, orientation, texture, material, combinations thereof, and the like.

In some embodiments, a distance from the proximal end (510) of the cinch device (530) to the first fiducial (503) may be equal to a length of the first electrode of an electrode subset (e.g., three electrodes) of an ablation device. In some embodiments, a distance from the first fiducial (503) to the second fiducial (505) may correspond to a distance or separation between the first and second electrodes of the electrode subset of three electrodes. In some embodiments, a distance between the second fiducial (505) and a third fiducial (507) may correspond to a length of the second electrode of the electrode subset of three electrodes. In some embodiments, a distance from third fiducial (507) to fourth fiducial (512) may correspond to a distance or separation between the second electrode and the third electrode of an electrode subset of three electrodes. In some embodiments, a distance from fourth fiducial (512) to fifth fiducial (513) may be equal to a length of the third electrode of an electrode subset of three electrodes. In this illustrative example, the set of fiducials on each lumen of the cinch device (530) may correspond to an electrode triplet of an ablation device configured to extend through the cinch device (530).

In some embodiments, an ablation device and cinch device each having fiducials may be used to improve determination of a location of the electrodes relative to each lumen of the cinch device. For example, the fiducials may be used to determine the fraction of an electrode subset disposed outside the cinch device for each lumen of the cinch device. For example such fiducials on the cinch device may be provided in conjunction with fiducials on the ablation device in the form of alternating bands as illustrated in FIG. 4 to assist with such a determination of the exposed fraction of electrode subsets outside of the cinch device. Once the number of electrode subsets in each lumen is determined, a signal generator may be configured to deliver energy to the electrodes looped around the pulmonary veins without delivering energy to electrodes within the cinch device. For example, a user may enter fiducial information into a user interface of the signal generator.

In some embodiments, verification using the fiducials on the ablation device and/or the cinch device that electrodes at the distal tip of the cinch device are suitably deployed (i.e., a majority of electrodes of an electrode group are deployed just outside the distal tip of the cinch device, for both distal and proximal tubes or lumens of the cinch device), the ablation device's position relative to the cinch device may be locked in place. In some embodiments, the ablation device may be held in place relative to the cinch device using a locking mechanism. For example, the ablation device may be held in place using a clip (e.g., a surgical clip) at a proximal end of the cinch device, surgical tape, combinations thereof, and the like. In some embodiments, a locking mechanism may be engaged after a predetermined number of electrodes of an electrode group are disposed distal to a cinch device (e.g., majority of electrodes of an electrode subset are deployed outside of a distal end of a first and second lumen of the cinch device).

In this manner, the electrodes disposed along the ablation device in a loop may be firmly positioned around a set of four pulmonary veins. Pulsed electric field ablation energy may be delivered to suitable electrode sets or pairings (e.g., exposed electrodes around the loop) in order to rapidly ablate tissue around the pulmonary veins (e.g., create a box lesion). This method of delivering a box lesion may be useful, for example, as a therapeutic treatment for one or more cardiac arrhythmia conditions such as atrial fibrillation.

Pulsed electric field voltage pulses with a suitable voltage level (such as in the kilo-Volt range) may be delivered in the form of a suitable waveform as described herein. The waveforms may have a hierarchical structure with a multiplicity of levels of hierarchy as suitable for efficient and effective therapy delivery. As described in more detail herein, a signal generator may be configured to deliver a set of pulse waveforms to the ablation device. In some embodiments, the start of ablation delivery may occur in timed synchrony with a set of pacing pulses (e.g., during refractory periods associated with the set of pacing pulses).

The electrodes as described may be composed of any suitable biocompatible conductive material including, but not limited to, one or more of silver, palladium, stainless steel, platinum, titanium, platinum-iridium alloys, gold, copper, nickel, combinations thereof, and the like. In some embodiments, the electrode materials may be plated, coated, and/or otherwise applied in an appropriately thick layer on top of a different substrate material. In some embodiments, electrode portions may be coupled using annealing, soldering, welding, crimping, lamination, combinations thereof, and the like. The spline, loop, and body of the ablation devices disclosed may be composed of any suitable biocompatible material including metals, glasses, ceramics, polymers, combinations thereof, and the like. The catheter shaft may be made of a flexible polymeric material such as Teflon, Nylon, Pebax, combinations thereof, and the like.

In the embodiments described in the foregoing and without limitation, the ablation device itself may be a steerable device with pull wires for controlling deflection through a suitable mechanism in the catheter handle, as is known to those skilled in the art.

II. Methods

Also described here are methods for ablating tissue (e.g., heart tissue) using the systems and devices described above. An ablation device may be introduced into an epicardial space. The ablation catheter may be advanced through a cinch device and looped around cardiac tissue such as a set of pulmonary veins. The distal end of the ablation catheter may be advanced back through the cinch device such that the ends of the ablation catheter may be pulled away from the cinch device such that the loop of the ablation catheter tightens around the tissue to increase contact and apply a predetermined force. In some embodiments, a position of the ablation catheter relative to the cinch device may be verified using a set of fiducials disposed on the ablation catheter and/or cinch device. Energy delivery to a set of electrodes of the ablation catheter may be based on the electrodes identified using the fiducials. For example, a pulse waveform may be generated and delivered to one or more identified electrodes of the ablation catheter (e.g., electrodes exposed outside the cinch device) to ablate tissue.

Generally, the methods described here include introducing and disposing an ablation device through a cinch device and looped around one or more pulmonary veins. Once the proximal and distal ends of the ablation device are disposed proximal to the cinch device, the cinch device may be positioned and the ends of the ablation device may be drawn through the cinch device such that the loop formed by the ablation device is tightened around a set of pulmonary veins to ablate. The position of the ablation device relative to the cinch device may be locked in place. A pulse waveform may be delivered by one or more electrodes of the ablation device to ablate tissue. In some embodiments, the pulse waveforms may include a set of levels of a hierarchy to reduce total energy delivery. It should be appreciated that any of the ablation devices described herein may be used to ablate tissue using the methods discussed below as appropriate.

Figure 16:
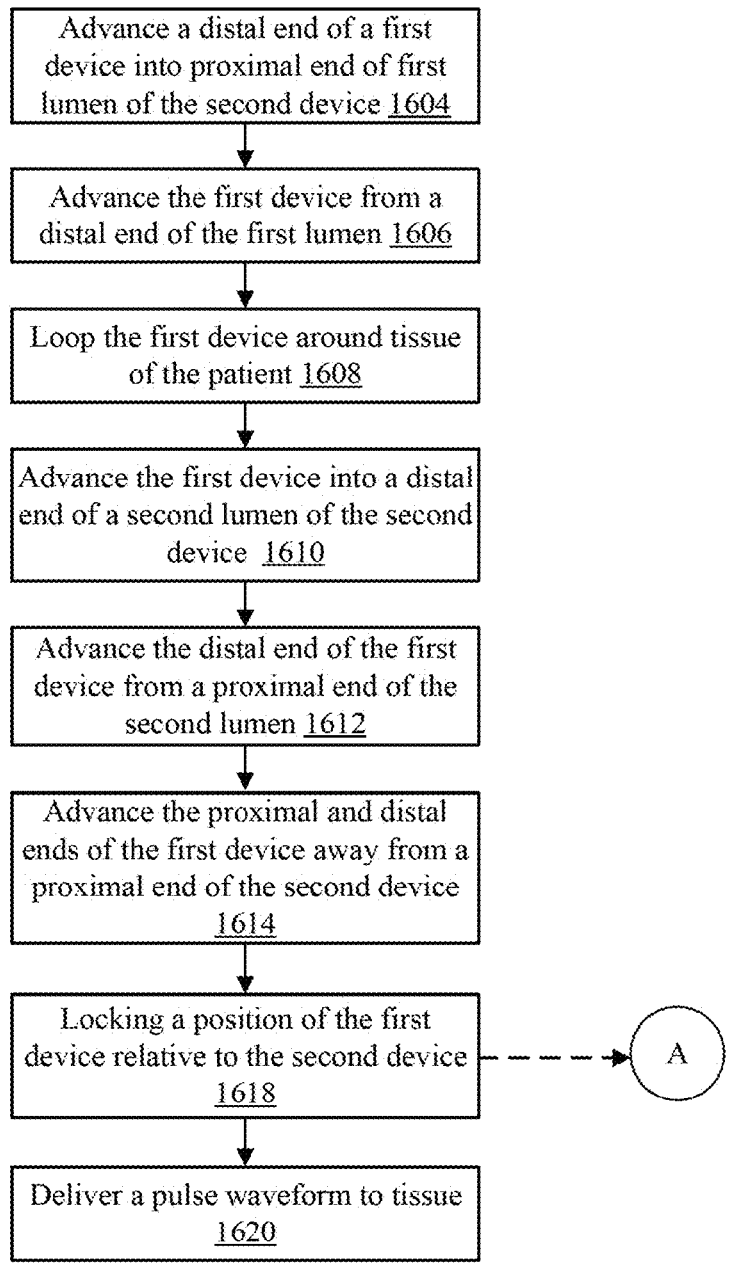
FIG. 16 illustrates a method for positioning an ablation catheter relative to tissue of a patient, according to embodiments.

As a non-limiting example, in some embodiments, a system can include one or more ablation devices (e.g., an ablation device as illustrated and described with respect to FIGS. 1-7, 14, and 15) useful for ablating tissue. FIG. 16 is a flowchart (1600) of an example method of a tissue ablation process. A distal end of a first device may be advanced into a proximal end of a first lumen of a second device (e.g., cinch device), at (1604). The first device (e.g., ablation device, such as the ablation device (102) may be any of the ablation devices (15, 102, 202, 302, 402, 602, 702, 840, 1501) described herein. The first device may be advanced through the first lumen and out from a distal end of the first lumen of the cinch device, at (1606). The first device may be looped around tissue of the patient, at (1608). For example, the ablation device may extend from a distal end of the cinch device and be looped around tissue, such as a set of four pulmonary veins, at the base of the trunk of the veins. In some embodiments, pericardial reflections or folds in the pericardial membrane may be excised to permit such looping.

The first device may be advanced back into the first device through a proximal end of a second lumen, at (1610). A portion of the first device may be disposed in the first lumen while a more distal portion of the first device is disposed and/or advanced into the second lumen of the second device. The first device may be advanced through the second lumen and out from a proximal end of the second lumen of the cinch device, at (1612). A proximal and distal end of the ablation device may extend from a proximal end of the cinch device. The cinch device may be angled obliquely with respect to the patient chest. The proximal and distal ends of the first device may be advanced away from a proximal end of the second device, at (1614). For example, the proximal and distal ends of the ablation device are drawn through the cinch device until the loop of the ablation device contacts and firmly encircles all the pulmonary veins. In this manner, the loop formed by a central portion of the ablation device may bend (e.g., form a noose) around the pulmonary veins. Alternatively, the ablation device may first be looped around the set of four pulmonary veins and then the proximal and distal ends of the ablation device may be advanced through the two lumens of the cinch device. For example, the cinch device may be advanced over the ablation device in a distal direction towards the heart after the ablation device is looped around tissue. A user may draw the ablation device away a predetermined amount to increase contact between the ablation device and tissue and/or to apply a predetermined amount of force from the ablation device to the tissue. Depending on the size of the left atrium, one or more of the electrodes of the ablation device may be drawn into the cinch device as the loop is tightened around the pulmonary veins. The electrodes exposed on the loop may be used to deliver ablation energy to tissue.

In some embodiments, prior to advancing a distal end of a first device into the proximal end of the first lumen of the second device, at (1604), a guidewire may be positioned around cardiac tissue (e.g., one or more pulmonary veins of the heart), using procedures and methods as described in the '394 PCT Application Publication. The ends of the guidewire may be placed within the second device (e.g., the cinch device), and then the first device (e.g., the ablation device) may be passed over the guidewire such that its distal end is advanced through the proximal end of the first lumen of the second device, at (1604). In some embodiments, prior to advancing the first device through the second device, at (1604), a distal end of the second device can be advanced into an open pericardial space of a patient at a location that permits access to the posterior section of the left atrium. Alternatively, once the first device has been advanced through the first and second lumens of the second device, at (1614), the distal end of the second device may be advanced into the open pericardial space. While the distal end of the second device can be advanced into the pericardial space, the proximal end of the second device can remain external to the heart and/or the patient.

In some embodiments, a guidewire may be advanced through the first device (e.g., the ablation device) such that the first device and the guidewire may be collectively advanced through a first lumen of the second device (e.g., cinch device) so as to encircle the pulmonary veins and posterior wall of the left atrium and then drawn back through a second lumen of the second device. The placement of the first device and/or second device may be by way of any of subxiphoid access, thoracotomy, and direct open chest access.

Figure 17:
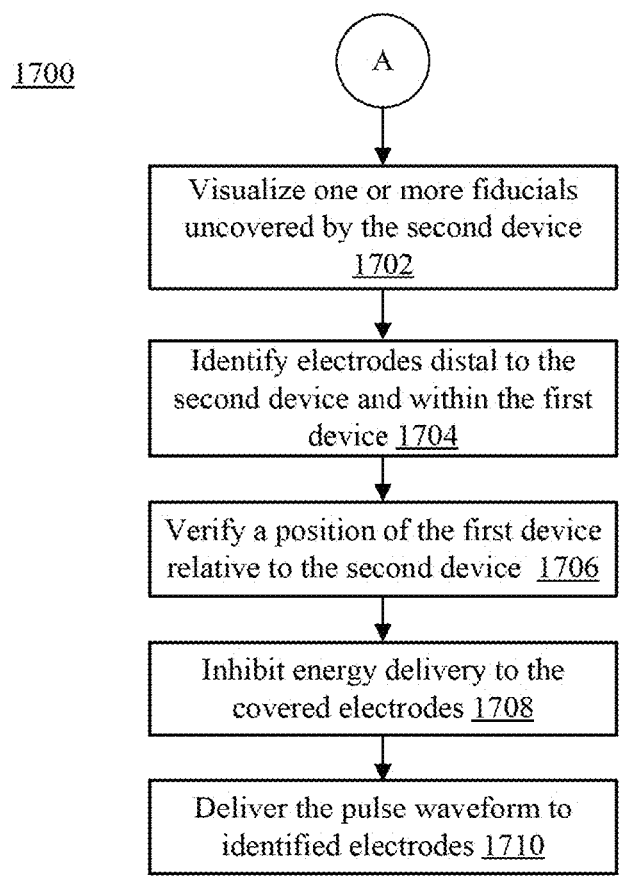
FIG. 17 illustrates a method for verifying ablation catheter positioning, according to embodiments.

In some embodiments, the process may proceed from (1614) to the flowchart (1700) of FIG. 17 described in more detail herein, where a user (e.g., surgeon) may view one or more sets of fiducials on one or more of the ablation device and cinch device to determine the location of the electrodes relative to the cinch device (e.g., number of electrodes within the first and second lumens of the cinch device). In some embodiments, a position of the first device may be locked relative to the second device, at (1618). For example, a lock such as a clip may be used to hold the cinch device at a fixed position relative to the ablation device such that a user holding one of the cinch device and ablation device may keep the other device in a relative fixed position. The user may verify that the positioning of the first device relative to the tissue. For example, the user may identify and select the electrodes of the first device to receive ablation energy and conversely inhibit energy delivery to the electrodes covered by the second device. A pulse waveform may be delivered to tissue through a set of electrodes of the first device, at (1620).

In some embodiments, the set of electrodes may be configured in a set of anode-cathode pairings. In some embodiments, the electrodes or an appropriate sequence of paired anode-cathode subsets of electrodes may be electrically activated in a sequential manner to deliver a pulse waveform with each anode-cathode pairing. For example, the set of electrodes may be activated sequentially in a clockwise or counter-clockwise manner. As another example, the cathode electrodes may be activated sequentially along with respective sequential anode electrodes activation until ablation is completed. The electrodes may be activated all at once or in a predetermined sequence. The sequential activation pattern may occur over the entire set of paired anode-cathode subsets during a single heartbeat, or over a portion of the set of paired anode-cathode subsets during a single heartbeat. In general, such activation for ablation delivery may occur over a plurality of heartbeats.

In some embodiments, the electrodes may be independently addressable, and the electrodes may be energized in any sequence using any pulse waveform sufficient to ablate tissue by irreversible electroporation. In some embodiments, ablation may be delivered rapidly with all electrodes activated at the same time. A variety of such electrode pairing options exist and may be implemented based on the convenience thereof. In some embodiments, hierarchical voltage pulse waveforms having a nested structure and a hierarchy of time intervals as described herein may be useful for irreversible electroporation, providing control and selectivity in different tissue types. A pulse waveform may be generated by a signal generator (e.g., the signal generator (810)) and may include a set of levels in a hierarchy. A variety of hierarchical waveforms may be generated with a signal generator as disclosed herein. For example, the pulse waveform may include a first level of a hierarchy of the pulse waveform including a first set of pulses. Each pulse has a pulse time duration and a first time interval separating successive pulses. A second level of the hierarchy of the pulse waveform may include a plurality of first sets of pulses as a second set of pulses. A second time interval may separate successive first sets of pulses. The second time interval may be at least three times the duration of the first time interval. A third level of the hierarchy of the pulse waveform may include a plurality of second sets of pulses as a third set of pulses. A third time interval may separate successive second sets of pulses. The third time interval may be at least thirty times the duration of the second level time interval.

It is understood that while the examples herein identify separate monophasic and biphasic waveforms, it should be appreciated that combination waveforms, where some portions of the waveform hierarchy are monophasic while other portions are biphasic, may also be generated. A voltage pulse waveform having a hierarchical structure may be applied across different anode-cathode subsets (optionally with a time delay). The generated pulse waveform may be delivered to tissue. Accordingly, in some embodiments, a contiguous, transmural zone of ablated tissue may electrically isolate the pulmonary vein from a main body of the left atrium.

In some embodiments, a portion of an electrode subset may be distal to the cinch device. For delivery of ablation energy where a subset of electrodes are wired together, it may be desirable to have a majority of an electrode subset be disposed distal to the cinch device for delivery of ablation energy. Additionally or alternatively, fluoroscopy and/or other visualization device (e.g., endoscope and/or method may be used to visualize the position of the electrodes of the ablation device relative to the cinch device and/or confirm the steps being performed.

FIG. 17 is a flowchart (1700) of an example method of a verifying tissue ablation process. In some embodiments, the method (1700) may follow from any of the steps of FIG. 16. The method (1700) includes visualizing one or more fiducials uncovered by the second device, at (1702). For example, location of the electrodes may be automatically and/or manually identified based on visualized fiducials on an X-ray or fluoroscopic image obtained at an appropriate angulation. The electrodes distal to the second device and within the first device may be identified, at (1704). A position of the first device relative to the second device may be verified, at (1706). For example, a user may input the electrodes to activate and deactivate into a user interface coupled to a signal generator. Energy delivery to the covered electrodes may be inhibited, at (1708). A pulse waveform may be delivered to tissue through a set of electrodes of the first device, at (1710), in a similar manner to as described above in (1620).

Pulse Waveform

Disclosed herein are methods, systems and apparatuses for the selective and rapid application of pulsed electric fields/waveforms to effect tissue ablation with irreversible electroporation. The pulse waveform(s) as disclosed herein are usable with any of the systems (800), devices (e.g., 102, 202, 302, 402, 502, 602, 702, 840), and methods described herein. Some embodiments are directed to pulsed high voltage waveforms together with a sequenced delivery scheme for delivering energy to tissue via sets of electrodes. In some embodiments, peak electric field values can be reduced and/or minimized while at the same time sufficiently large electric field magnitudes can be maintained in regions where tissue ablation is desired. This also reduces the likelihood of excessive tissue damage or the generation of electrical arcing, and locally high temperature increases. In some embodiments, a system useful for irreversible electroporation includes a signal generator and a processor capable of being configured to apply pulsed voltage waveforms to a selected plurality or a subset of electrodes of an ablation device. In some embodiments, the processor is configured to control inputs whereby selected pairs of anode-cathode subsets of electrodes can be sequentially triggered based on a pre-determined sequence.

In some embodiments, the pulsed voltage waveforms disclosed herein are hierarchical in organization and have a nested structure. In some embodiments, the pulsed waveform includes hierarchical groupings of pulses with a variety of associated timescales. Furthermore, the associated timescales and pulse widths, and the numbers of pulses and hierarchical groupings, can be selected so as to satisfy one or more of a set of Diophantine inequalities.

Pulsed waveforms for electroporation energy delivery as disclosed herein may enhance the safety, efficiency and effectiveness of the energy delivery by reducing the electric field threshold associated with irreversible electroporation, yielding more effective ablative lesions with reduced total energy delivered.

Figure 10:
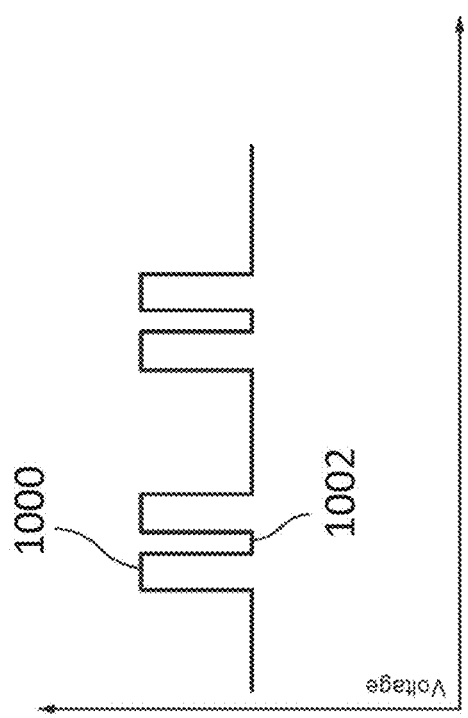
FIG. 10 is an example waveform including a sequence of voltage pulses with a pulse width defined for each pulse, according to embodiments.

FIG. 10 illustrates a pulsed voltage waveform in the form of a sequence of rectangular double pulses, with each pulse, such as the pulse (1000) being associated with a pulse width or duration. The pulse width/duration can be about 0.5 microseconds, about 1 microsecond, about 5 microseconds, about 10 microseconds, about 25 microseconds, about 50 microseconds, about 100 microseconds, about 125 microseconds, about 140 microseconds, about 150 microseconds, including all values and sub-ranges in between. The pulsed waveform of FIG. 10 illustrates a set of monophasic pulses where the polarities of all the pulses are the same (all positive in FIG. 10, as measured from a zero baseline). In some embodiments, such as for irreversible electroporation applications, the height of each pulse (1000) or the voltage amplitude of the pulse (1000) can be in the range from about 400 volts, about 1,000 volts, about 5,000 volts, about 10,000 volts, about 15,000 volts, including all values and sub ranges in between. As illustrated in FIG. 10, the pulse (1000) is separated from a neighboring pulse by a time interval (1002), also sometimes referred to as a first time interval. The first time interval can be about 10 microseconds, about 50 microseconds, about 100 microseconds, about 200 microseconds, about 500 microseconds, about 800 microseconds, about 1 millisecond including all values and sub ranges in between, in order to generate irreversible electroporation.

Figure 11:
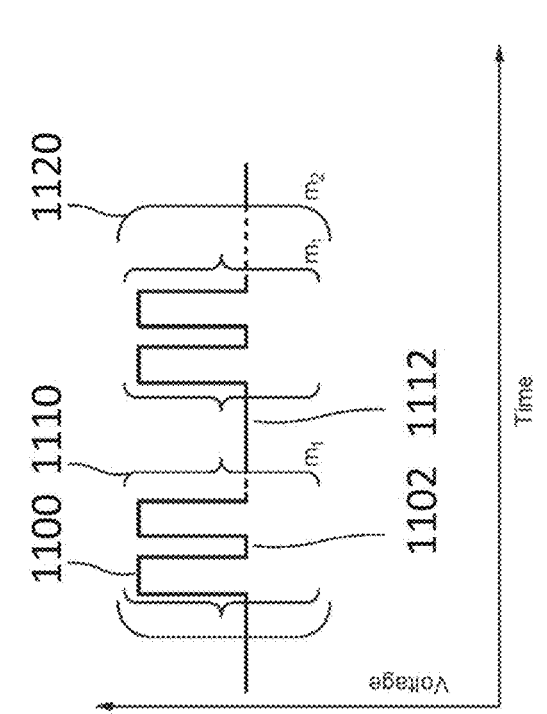
FIG. 11 schematically illustrates a hierarchy of pulses including pulse widths, intervals between pulses, and groupings of pulses, according to embodiments.

FIG. 11 introduces a pulse waveform with the structure of a hierarchy of nested pulses. FIG. 11 shows a series of monophasic pulses such as pulse (1100) with pulse width/pulse time duration w, separated by a time interval (also sometimes referred to as a first time interval) such as (1102) of duration $t_1$ between successive pulses, a number $m_1$ of which are arranged to form a group of pulses (1110) (also sometimes referred to as a first set of pulses). Furthermore, the waveform has a number $m_2$ of such groups of pulses (also sometimes referred to as a second set of pulses) separated by a time interval (1112) (also sometimes referred to as a second time interval) of duration $t_2$ between successive groups. The collection of $m_2$ such pulse groups, marked by (1120) in FIG. 11, constitutes the next level of the hierarchy, which can be referred to as a packet and/or as a third set of pulses. The pulse width and the time interval $t_1$ between pulses can both be in the range of microseconds to hundreds of microseconds, including all values and sub ranges in between. In some embodiments, the time interval $t_2$ can be at least three times larger than the time interval $t_1$. In some embodiments, the ratio $t_2/t_1$ can be in the range between about 3 and about 300, including all values and sub-ranges in between.

Figure 12:
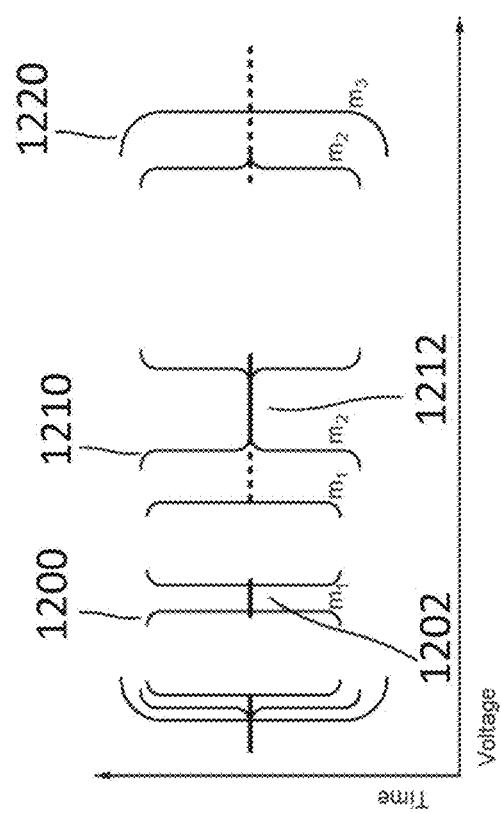
FIG. 12 provides a schematic illustration of a nested hierarchy of monophasic pulses displaying different levels of nested hierarchy, according to embodiments.

FIG. 12 further elaborates the structure of a nested pulse hierarchy waveform. In this figure, a series of $m_1$ pulses (individual pulses not shown) form a group of pulses (1200) (e.g., a first set of pulses). A series of $m_2$ such groups separated by an inter-group time interval (1210) of duration $t_2$ (e.g., a second time interval) between one group and the next form a packet (e.g., a second set of pulses). A series of $m_3$ such packets separated by time intervals (1212) of duration $t_3$ (e.g., a third time interval) between one packet and the next form the next level in the hierarchy, a super-packet labeled (1220) (e.g., a third set of pulses) in the figure. In some embodiments, the time interval $t_3$ can be at least about thirty times larger than the time interval $t_2$. In some embodiments, the time interval $t_3$ can be at least fifty times larger than the time interval $t_2$. In some embodiments, the ratio $t_3/t_2$ can be in the range between about 30 and about 800, including all values and sub-ranges in between. The amplitude of the individual voltage pulses in the pulse hierarchy can be anywhere in the range from 500 volts to 7,000 volts or higher, including all values and sub ranges in between.

Figure 13:
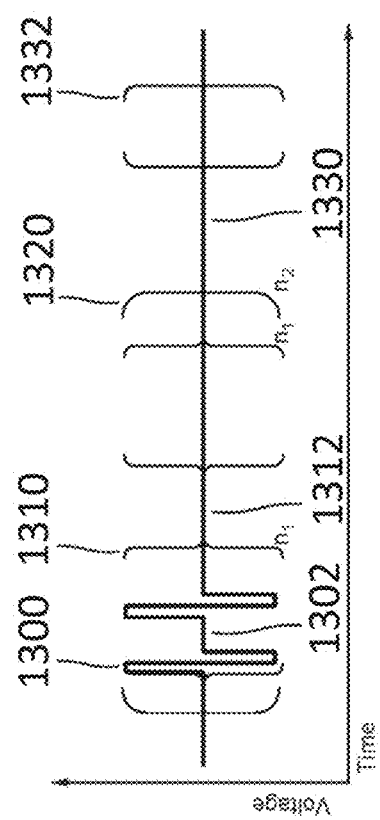
FIG. 13 is a schematic illustration of a nested hierarchy of biphasic pulses displaying different levels of a nested hierarchy, according to embodiments.

FIG. 13 provides an example of a biphasic waveform sequence with a hierarchical structure. In the example shown in the figure, biphasic pulses such as (1300) have a positive voltage portion as well as a negative voltage portion to complete one cycle of the pulse. There is a time delay (1302) (e.g., a first time interval) between adjacent cycles of duration $t_1$, and $n_1$ such cycles form a group of pulses (1310) (e.g., a first set of pulses). A series of $n_2$ such groups separated by an inter-group time interval (1312) (e.g., a second time interval) of duration $t_2$ between one group and the next form a packet (1320) (e.g., a second set of pulses). The figure also shows a second packet (1330), with a time delay (1332) (e.g., a third time interval) of duration $t_3$ between the packets. Just as for monophasic pulses, higher levels of the hierarchical structure can be formed as well. The amplitude of each pulse or the voltage amplitude of the biphasic pulse can be anywhere in the range from 500 volts to 7,000 volts or higher, including all values and sub ranges in between. The pulse width/pulse time duration can be in the range from nanoseconds or even sub-nanoseconds to tens of microseconds, while the delays $t_1$ can be in the range from zero to several microseconds. The inter-group time interval $t_2$ can be at least ten times larger than the pulse width. In some embodiments, the time interval $t_3$ can be at least about twenty times larger than the time interval $t_2$. In some embodiments, the time interval $t_3$ can be at least fifty times larger than the time interval $t_2$.

Embodiments disclosed herein include waveforms structured as hierarchical waveforms that include waveform elements/pulses at various levels of the hierarchy. The individual pulses such as (1100) in FIG. 11 includes the first level of the hierarchy, and have an associated pulse time duration and a first time interval between successive pulses. A set of pulses, or elements of the first level structure, form a second level of the hierarchy such as the group of pulses/second set of pulses (1110) in FIG. 11. Among other parameters, associated with the waveform are parameters such as a total time duration of the second set of pulses (not shown), a total number of first level elements/first set of pulses, and second time intervals between successive first level elements that describe the second level structure/second set of pulses. In some embodiments, the total time duration of the second set of pulses can be between about 20 microseconds and about 10 milliseconds, including all values and subranges in between. A set of groups, second set of pulses, or elements of the second level structure, form a third level of the hierarchy such as the packet of groups/third set of pulses (1120) in FIG. 11. Among other parameters, there is a total time duration of the third set of pulses (not shown), a total number of second level elements/second set of pulses, and third time intervals between successive second level elements that describe the third level structure/third set of pulses. In some embodiments, the total time duration of the third set of pulses can be between about 60 microseconds and about 200 milliseconds, including all values and sub ranges in between. The generally iterative or nested structure of the waveforms can continue to a higher plurality of levels, such as ten levels of structure, or more.

In some embodiments, hierarchical waveforms with a nested structure and hierarchy of time intervals as described herein are useful for irreversible electroporation ablation energy delivery, providing a good degree of control and selectivity for applications in different tissue types. A variety of hierarchical waveforms can be generated with a suitable pulse generator. It is understood that while the examples herein identify separate monophasic and biphasic waveforms for clarity, it should be noted that combination waveforms, where some portions of the waveform hierarchy are monophasic while other portions are biphasic, can also be generated/implemented.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

As used in this specification, the singular forms "a," "an" and "the" include plural referents unless the context clearly dictates otherwise. Thus, for example, the term "a member" is intended to mean a single member or a combination of members, "a material" is intended to mean one or more materials, "a processor" is intended to mean a single processor or multiple processors; and "memory" is intended to mean one or more memories, or a combination thereof.

As used herein, the terms "about" and "approximately" generally mean plus or minus 10% of the value stated. For example, about 0.5 would include 0.45 and 0.55, about 10 would include 9 to 11, about 1000 would include 900 to 1100.

The specific examples and descriptions herein are exemplary in nature and embodiments may be developed by those skilled in the art based on the material taught herein without departing from the scope of the present invention, which is limited only by the attached claims.

We claim:

1. A system, comprising:
an ablation device including a proximal portion, a distal portion, and a central portion, the central portion including a set of electrodes disposed thereon,
the set of electrodes includes subsets of electrodes, each subset of electrodes having a first length and adjacent subsets of electrodes being spaced from each other by a second length,
the ablation device including first and second sets of fiducials, fiducials of the first and second sets of fiducials being alternately disposed along a length of the ablation device, the first set of fiducials differing from the second set of fiducials by one or more characteristics, and adjacent fiducials of the first set of fiducials being spaced apart by a sum of the first and second lengths; and a cinch device defining a first lumen configured to slidably receive the proximal portion of the ablation device and a second lumen extending parallel to the first lumen and configured to slidably receive the distal portion of the ablation device, such that the central portion of the ablation device forms an adjustable loop when the proximal and distal portions of the ablation device are received in the first and second lumens of the cinch device.

2. The system of claim 1, wherein the set of electrodes includes between about 4 electrode subsets and about 20 electrode subsets.

3. The system of claim 1, wherein the first and second set of fiducials are disposed along at least one of the proximal and distal portions of the ablation device.

4. The system of claim 1, wherein the one or more characteristics include at least one of: a length, a thickness, a depth, a shape, a color, a pattern, an orientation, a texture, or a material.

5. The system of claim 1, wherein the cinch device has a length that is an integer multiple of a sum of the first and second lengths.

6. The system of claim 1, wherein the ablation device is configured to transition between a first configuration in which the ablation device extends linearly and a second configuration in which the central portion of the ablation device forms the adjustable loop.

7. The system of claim 1, wherein the adjustable loop is configured to be positioned around a set of pulmonary veins of a heart.

8. The system of claim 1, wherein the set of electrodes are configured to generate a pulsed electric field to ablate cardiac tissue in response to receiving a voltage pulse waveform.

9. The system of claim 1, wherein the ablation device includes a handle coupled to a proximal end of the proximal portion of the ablation device.

10. The system of claim 1, wherein the ablation device is a catheter including a guidewire lumen configured to receive a guidewire, such that the catheter can be positioned around a set of pulmonary veins of a heart using a guidewire.

11. The system of claim 1, further comprising a lock configured to hold the ablation device in place relative to the cinch device.

12. The system of claim 1, wherein each electrode of the set of electrodes includes a length of between about 1 mm and about 12 mm.

13. The system of claim 1, wherein the distal portion of the ablation device has a length of between about 20 cm and about 70 cm.

14. A system, comprising:
an ablation device including a proximal portion, a distal portion, and a central portion, the central portion including a set of electrodes disposed thereon,
the set of electrodes includes subsets of electrodes, each subset of electrodes having a first length and adjacent subsets of electrodes being spaced from each other by a second length,
the ablation device including first and second sets of fiducials, fiducials of the first and second sets of fiducials being alternately disposed along a length of the ablation device, the first set of fiducials differs from the second set of fiducials by one or more characteristics, and a fiducial of the first set of fiducials is spaced from an adjacent fiducial of the second set of fiducials by a third length equal to a width of an electrode of the set of electrodes; and a cinch device defining a first lumen configured to slidably receive the proximal portion of the ablation device and a second lumen extending parallel to the first lumen and configured to slidably receive the distal portion of the ablation device, such that the central portion of the ablation device forms an adjustable loop when the proximal and distal portions of the ablation device are received in the first and second lumens of the cinch device.

15. The system of claim 14, wherein the first and second set of fiducials are disposed along at least one of the proximal and distal portions of the ablation device.

16. The system of claim 14, wherein the one or more characteristics include at least one of: a length, a thickness, a depth, a shape, a color, a pattern, an orientation, a texture, or a material.

17. The system of claim 14, wherein the cinch device has a length that is an integer multiple of a sum of the first and second lengths.

18. The system of claim 17, wherein the ablation device is configured to transition between a first configuration in which the ablation device extends linearly and a second configuration in which the central portion of the ablation device forms the adjustable loop.

19. The system of claim 17, wherein the adjustable loop is configured to be positioned around a set of pulmonary veins of a heart.

20. The system of claim 17, wherein the set of electrodes are configured to generate a pulsed electric field to ablate cardiac tissue in response to receiving a voltage pulse waveform.

21. A system, comprising:
an ablation device including a proximal portion, a distal portion, and a central portion, the central portion including a set of electrodes disposed thereon,
the set of electrodes includes subsets of electrodes, each subset of electrodes having a first length and adjacent subsets of electrodes being spaced from each other by a second length, each subset of electrodes including a plurality of electrodes, and each electrode of the plurality of electrodes having a third length and being spaced from an adjacent electrode of the plurality of electrodes by a distance,
the ablation device including a set of fiducials with spacing between adjacent proximal fiducials alternating between a fourth length equal to the third length and a fifth length equal to the distance; and
a cinch device defining a first lumen configured to slidably receive the proximal portion of the ablation device and a second lumen extending parallel to the first lumen and configured to slidably receive the distal portion of the ablation device, such that the central portion of the ablation device forms an adjustable loop when the proximal and distal portions of the ablation device are received in the first and second lumens of the cinch device.

22. The system of claim 21, wherein the set of electrodes includes between about 4 electrode subsets and about 20 electrode subsets.

23. The system of claim 21, wherein the ablation device is configured to transition between a first configuration in which the ablation device extends linearly and a second configuration in which the central portion of the ablation device forms the adjustable loop.

24. The system of claim 21, wherein the adjustable loop is configured to be positioned around a set of pulmonary veins of a heart.

25. The system of claim 21, wherein the set of electrodes are configured to generate a pulsed electric field to ablate cardiac tissue in response to receiving a voltage pulse waveform.

26. A system, comprising:
an ablation device including a proximal portion, a distal portion, and a central portion, the central portion including a set of electrodes disposed thereon,
the set of electrodes includes subsets of electrodes, each subset of electrodes having a first length and adjacent subsets of electrodes being spaced from each other by a second length, each subset of electrodes including a plurality of electrodes, and a first electrode of the plurality of electrodes having a third length and a second electrode of the plurality of electrodes having a fourth length greater than the third length,
the ablation device including first and second sets of fiducials alternately disposed along a length of the ablation device, with a fiducial of the first set of fiducials being spaced from an adjacent fiducial of the second set of fiducials by the third length; and
a cinch device defining a first lumen configured to slidably receive the proximal portion of the ablation device and a second lumen extending parallel to the first lumen and configured to slidably receive the distal portion of the ablation device, such that the central portion of the ablation device forms an adjustable loop when the proximal and distal portions of the ablation device are received in the first and second lumens of the cinch device.

27. The system of claim 26, wherein the set of electrodes includes between about 4 electrode subsets and about 20 electrode subsets.

28. The system of claim 26, wherein the ablation device is configured to transition between a first configuration in which the ablation device extends linearly and a second configuration in which the central portion of the ablation device forms the adjustable loop.

29. The system of claim 26, wherein the adjustable loop is configured to be positioned around a set of pulmonary veins of a heart.

30. The system of claim 26, wherein the set of electrodes are configured to generate a pulsed electric field to ablate cardiac tissue in response to receiving a voltage pulse waveform.

* * * * *